United States Patent
Idelevich et al.

(10) Patent No.: US 10,363,263 B2
(45) Date of Patent: *Jul. 30, 2019

(54) ANTI-AGING COMPOSITIONS AND METHODS FOR USING SAME

(71) Applicant: Prescient Pharma LLC, Canton, MA (US)

(72) Inventors: Pavel Idelevich, Canton, MA (US); Anna Idelevich, Canton, MA (US)

(73) Assignee: Prescient Pharma, LLC, Canton, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 15/342,815

(22) Filed: Nov. 3, 2016

(65) Prior Publication Data

US 2017/0182075 A1   Jun. 29, 2017

Related U.S. Application Data

(60) Provisional application No. 62/250,910, filed on Nov. 4, 2015.

(51) Int. Cl.
| | | |
|---|---|---|
| *A61K 31/704* | (2006.01) | |
| *A61K 33/00* | (2006.01) | |
| *A61K 8/37* | (2006.01) | |
| *A61K 8/19* | (2006.01) | |
| *A61K 8/63* | (2006.01) | |
| *A61K 33/14* | (2006.01) | |
| *A61Q 19/08* | (2006.01) | |
| *A61K 31/191* | (2006.01) | |
| *A61K 31/194* | (2006.01) | |
| *A61K 31/203* | (2006.01) | |
| *A61P 9/10* | (2006.01) | |
| *A61P 9/12* | (2006.01) | |
| *A61P 19/10* | (2006.01) | |
| *A61P 25/28* | (2006.01) | |
| *A61P 35/00* | (2006.01) | |
| *A61P 37/00* | (2006.01) | |
| *A61K 8/20* | (2006.01) | |

(52) U.S. Cl.
CPC ............. *A61K 31/704* (2013.01); *A61K 8/19* (2013.01); *A61K 8/20* (2013.01); *A61K 8/37* (2013.01); *A61K 8/63* (2013.01); *A61K 33/00* (2013.01); *A61K 33/14* (2013.01); *A61P 9/10* (2018.01); *A61P 9/12* (2018.01); *A61P 19/10* (2018.01); *A61P 25/28* (2018.01); *A61P 35/00* (2018.01); *A61P 37/00* (2018.01); *A61Q 19/08* (2013.01); *A61K 31/191* (2013.01); *A61K 31/194* (2013.01); *A61K 31/203* (2013.01); *A61K 2300/00* (2013.01)

(58) Field of Classification Search
None
See application file for complete search history.

(56) References Cited

U.S. PATENT DOCUMENTS

| | | | |
|---|---|---|---|
| 6,355,410 | B1 | 3/2002 | Rich |
| 7,241,570 | B2 | 7/2007 | Prescott et al. |
| 7,482,134 | B2 | 1/2009 | Jang et al. |
| 8,455,515 | B2 | 6/2013 | Lang |
| 8,546,102 | B2 | 10/2013 | Licher et al. |
| 8,598,145 | B2 | 12/2013 | Ralph et al. |
| 9,066,923 | B2 | 6/2015 | Alkon |
| 2002/0169176 | A1* | 11/2002 | Elder .................. A61K 8/4953 514/262.1 |
| 2003/0104427 | A1 | 6/2003 | Petrini et al. |
| 2005/0123628 | A1* | 6/2005 | Zabrecky ............. A61K 31/352 424/725 |
| 2006/0008908 | A1 | 1/2006 | Giles |
| 2006/0229265 | A1 | 10/2006 | Milburn et al. |
| 2008/0020041 | A1 | 1/2008 | Ayres |
| 2008/0152734 | A1* | 6/2008 | Miyake ................ A61K 31/122 424/757 |
| 2011/0130748 | A1* | 6/2011 | Kellogg ............... A61B 18/203 606/9 |

(Continued)

FOREIGN PATENT DOCUMENTS

| | | | |
|---|---|---|---|
| CN | 101239096 | * | 8/2008 |
| CN | 105616839 | * | 6/2016 |
| EP | 207516 A1 | | 1/1987 |
| WO | 9704761 A1 | | 2/1997 |
| WO | 03090665 A2 | | 11/2003 |
| WO | 2007127809 A2 | | 11/2007 |
| WO | WO 2010133015 | * | 11/2010 |

OTHER PUBLICATIONS

English Machine Translation of CN 101239096 [online]. Espacenet, retrieved on Oct. 12, 2017. Retrieved from the internet: <www.espacenet.com>.*

English Machine Translation of CN 105616839 [online]. Espacenet, retrieved on Oct. 12, 2017. Retrieved from the internet: <www.espacenet.com>.*

(Continued)

*Primary Examiner* — Katherine Peebles
(74) *Attorney, Agent, or Firm* — Bekiares Eliezer LLP

(57) ABSTRACT

The invention generally relates to anti-aging compositions and methods for using the anti-aging compositions. In one aspect, the invention provides a method for preventing cellular aging in a cell of a subject, the method comprising the step of providing to the cell an effective amount of at least one lithium compound or a pharmaceutically acceptable salt thereof, and an effective amount of at least one glycyrrhizie triterpenoid compound or a pharmaceutically acceptable salt thereof, thereby preventing the cell from aging. This abstract is intended as a scanning tool for purposes of searching in the particular art and is not intended to be limiting of the present invention.

12 Claims, 13 Drawing Sheets
(1 of 13 Drawing Sheet(s) Filed in Color)

Specification includes a Sequence Listing.

(56) References Cited

U.S. PATENT DOCUMENTS

| | | | |
|---|---|---|---|
| 2012/0231089 A1* | 9/2012 | Vinitsky | A61K 31/525 424/643 |
| 2013/0064803 A1* | 3/2013 | Naidu | A61K 45/06 424/94.6 |
| 2014/0255424 A1 | 9/2014 | Wyss-Coray et al. | |
| 2015/0050713 A1 | 2/2015 | Malakhov et al. | |

OTHER PUBLICATIONS

English machine translation of WO/2010/133015 [online]. WIPO, 2010. [retrieved on Apr. 13, 2018]. retrieved from the internet: <https://patentscope.wipo.int/search/en/search.jsf>. (Year: 2018).*

Mahnensmith et al. The Plasma Membrane Sodium-Hydrogen Exchanger and its Role in Physiological and Pathophysiological Processes. Circulation Research. 1985; 56: 773-788.

Fliegel et al. Phosphorylation of the C-terminal domain of the Na+/H+ exchanger by Ca2+/calmodulin-dependent protein kinase II. Biochem. J. 139 (1992) 282, 139-145.

Garnovskaya et al. Rapid activation of sodium-proton exchange and extracellular signal regulated protein kinase in fibroblasts by G protein-coupled 5-HT1A receptor involves distinct signalling cascades. Biochem. J. (1998) 330, 489-495.

Slepkov et al. Structural and functional analysis of the Na+/H+ exchanger. Biochemical Journal Feb. 1, 2007, 401 (3) 623-633.

Merida et al. Diacylglycerol kinases: at the hub of cell signaling. Biochem. J. (2008) 409, 1-18 (Printed in Great Britain).

Eckford et al. Targeting the regulation of CFTR channels. Biochem. J. (2011) 435, e1-e4.

Van et al. Dietary Omega-3 Polyunsaturated Fatty Acids Suppress NHE-1 Upregulation in a Rabbit Model of Volume- and Pressure-Overload, Front Physiol. 2012; 3: 76.

Dominguez et al. Diacylglycerol kinase α is a critical signaling node and novel therapeutic target in glioblastoma and other cancers. Cancer Discov. Jul. 2013; 3(7): 782-797.

Reshkin et al. Na+—H+ Exchanger, pH Regulation and Cancer. Recent Patents on Anti-Cancer Drug Discovery, vol. 8, No. 1, Jan. 2013, pp. 85-99(15).

International Search Report and Written Opinion for Intl. Pat. App. No. PCT/US2016/60371, dated Mar. 16, 2017, 17 pp.

* cited by examiner

SEQUENCE LISTING

```
<160> NUMBER OF SEQ ID NOS: 38

<210> SEQ ID NO 1
<211> LENGTH: 20
<212> TYPE: DNA
<213> ORGANISM: Artificial Sequence
<220> FEATURE:
<223> OTHER INFORMATION: Primer sequence

<400> SEQUENCE: 1
tctacaatga gctgcgtgtg                                              20

<210> SEQ ID NO 2
<211> LENGTH: 20
<212> TYPE: DNA
<213> ORGANISM: Artificial Sequence
<220> FEATURE:
<223> OTHER INFORMATION: Primer sequence

<400> SEQUENCE: 2
ttttcacggt tggccttagg                                              20

<210> SEQ ID NO 3
<211> LENGTH: 37
<212> TYPE: DNA
<213> ORGANISM: Artificial Sequence
```

```
<220> FEATURE:
<223> OTHER INFORMATION: Primer sequence

<400> SEQUENCE: 3
ggtttttgag ggtgagggtg agggtgaggg tgagggt                                37

<210> SEQ ID NO 4
<211> LENGTH: 39
<212> TYPE: DNA
<213> ORGANISM: Artificial Sequence
<220> FEATURE:
<223> OTHER INFORMATION: primer sequence

<400> SEQUENCE: 4
tcccgactat ccctatccct atccctatcc ctatccta                               39

<210> SEQ ID NO 5
<211> LENGTH: 23
<212> TYPE: DNA
<213> ORGANISM: Artificial Sequence
<220> FEATURE:
<223> OTHER INFORMATION: primer sequence

<400> SEQUENCE: 5
cagcaagtgg gaaggtgtaa tcc                                               23

<210> SEQ ID NO 6
<211> LENGTH: 25
<212> TYPE: DNA
<213> ORGANISM: artificial sequence
<220> FEATURE:
<223> OTHER INFORMATION: primer sequence

<400> SEQUENCE: 6
cccattctat catcaacggg tacaa                                             25

<210> SEQ ID NO 7
<211> LENGTH: 39
<212> TYPE: DNA
<213> ORGANISM: artificial sequence
<220> FEATURE:
<223> OTHER INFORMATION: primer sequence

<400> SEQUENCE: 7
cggtttgttt gggtttgggt ttggtttgg gtttgggtt                               39

<210> SEQ ID NO 8
<211> LENGTH: 39
<212> TYPE: DNA
<213> ORGANISM: artificial sequence
<220> FEATURE:
<223> OTHER INFORMATION: primer sequence

<400> SEQUENCE: 8
ggcttgcctt acccttaccc ttacccttac ccttaccct                              39

<210> SEQ ID NO 9
<211> LENGTH: 21
<212> TYPE: DNA
<213> ORGANISM: artificial sequence
<220> FEATURE:
<223> OTHER INFORMATION: primer sequence

<400> SEQUENCE: 9
actggtctag gacccgagaa g                                                 21
```

```
<210> SEQ ID NO 10
<211> LENGTH: 21
<212> TYPE: DNA
<213> ORGANISM: artificial sequence
<220> FEATURE:
<223> OTHER INFORMATION: primer sequence

<400> SEQUENCE: 10
tcaatggtgc ctctggagat t                                          21

<210> SEQ ID NO 11
<211> LENGTH: 19
<212> TYPE: DNA
<213> ORGANISM: artificial sequence
<220> FEATURE:
<223> OTHER INFORMATION: primer sequence

<400> SEQUENCE: 11
gcactttggt tgcccaatg                                             19

<210> SEQ ID NO 12
<211> LENGTH: 19
<212> TYPE: DNA
<213> ORGANISM: artificial sequence
<220> FEATURE:
<223> OTHER INFORMATION: primer sequence

<400> SEQUENCE: 12
gcacgtttct ctcgttgcg                                             19

<210> SEQ ID NO 13
<211> LENGTH: 22
<212> TYPE: DNA
<213> ORGANISM: artificial sequence
<220> FEATURE:
<223> OTHER INFORMATION: primer sequence

<400> SEQUENCE: 13
aaagaccgga agccattaca ag                                         22

<210> SEQ ID NO 14
<211> LENGTH: 23
<212> TYPE: DNA
<213> ORGANISM: artificial sequence
<220> FEATURE:
<223> OTHER INFORMATION: primer sequence

<400> SEQUENCE: 14
gccactgaga agtgtctaat tga                                        23

<210> SEQ ID NO 15
<211> LENGTH: 20
<212> TYPE: DNA
<213> ORGANISM: artificial sequence
<220> FEATURE:
<223> OTHER INFORMATION: primer sequence

<400> SEQUENCE: 15
ccgctgtttt tctcgctgac                                            20

<210> SEQ ID NO 16
<211> LENGTH: 20
<212> TYPE: DNA
<213> ORGANISM: artificial sequence
<220> FEATURE:
<223> OTHER INFORMATION: primer sequence
```

```
<400> SEQUENCE: 16
cctgcgctga cgtttgtttt                                              20

<210> SEQ ID NO 17
<211> LENGTH: 21
<212> TYPE: DNA
<213> ORGANISM: artificial sequence
<220> FEATURE:
<223> OTHER INFORMATION: primer sequence

<400> SEQUENCE: 17
actggctgat gagtgtgtac g                                            21

<210> SEQ ID NO 18
<211> LENGTH: 20
<212> TYPE: DNA
<213> ORGANISM: artificial sequence
<220> FEATURE:
<223> OTHER INFORMATION: primer sequence

<400> SEQUENCE: 18
tgctttgcaa cttgctccag                                              20

<210> SEQ ID NO 19
<211> LENGTH: 20
<212> TYPE: DNA
<213> ORGANISM: artificial sequence
<220> FEATURE:
<223> OTHER INFORMATION: primer sequence

<400> SEQUENCE: 19
tgccgaagca gcaaaaactg                                              20

<210> SEQ ID NO 20
<211> LENGTH: 21
<212> TYPE: DNA
<213> ORGANISM: artificial sequence
<220> FEATURE:
<223> OTHER INFORMATION: primer sequence

<400> SEQUENCE: 20
tgatcaactg aggagctgct g                                            21

<210> SEQ ID NO 21
<211> LENGTH: 20
<212> TYPE: DNA
<213> ORGANISM: artificial sequence
<220> FEATURE:
<223> OTHER INFORMATION: primer sequence

<400> SEQUENCE: 21
gcgctgtttt tctcgctgac                                              20

<210> SEQ ID NO 22
<211> LENGTH: 22
<212> TYPE: DNA
<213> ORGANISM: artificial sequence
<220> FEATURE:
<223> OTHER INFORMATION: primer sequence

<400> SEQUENCE: 22
tctagaatga acggtggaag gc                                           22

<210> SEQ ID NO 23
```

```
<211> LENGTH: 20
<212> TYPE: DNA
<213> ORGANISM: artificial sequence
<220> FEATURE:
<223> OTHER INFORMATION: primer sequence

<400> SEQUENCE: 23
ttgagaatgg acgctgcatc                                              20

<210> SEQ ID NO 24
<211> LENGTH: 22
<212> TYPE: DNA
<213> ORGANISM: artificial sequence
<220> FEATURE:
<223> OTHER INFORMATION: primer sequence

<400> SEQUENCE: 24
ttccatcagc tctcaactcc tg                                           22

<210> SEQ ID NO 25
<211> LENGTH: 20
<212> TYPE: DNA
<213> ORGANISM: artificial sequence
<220> FEATURE:
<223> OTHER INFORMATION: primer sequence

<400> SEQUENCE: 25
aggccaacaa caatgacagc                                              20

<210> SEQ ID NO 26
<211> LENGTH: 20
<212> TYPE: DNA
<213> ORGANISM: artificial sequence
<220> FEATURE:
<223> OTHER INFORMATION: primer sequence

<400> SEQUENCE: 26
aagcacagtc agatgcacag                                              20

<210> SEQ ID NO 27
<211> LENGTH: 20
<212> TYPE: DNA
<213> ORGANISM: artificial sequence
<220> FEATURE:
<223> OTHER INFORMATION: primer sequence

<400> SEQUENCE: 27
acaaaactgt ggctgttcgc                                              20

<210> SEQ ID NO 28
<211> LENGTH: 21
<212> TYPE: DNA
<213> ORGANISM: artificial sequence
<220> FEATURE:
<223> OTHER INFORMATION: primer sequence

<400> SEQUENCE: 28
tgggatgtcc tctttctgca c                                            21

<210> SEQ ID NO 29
<211> LENGTH: 20
<212> TYPE: DNA
<213> ORGANISM: artificial sequence
<220> FEATURE:
<223> OTHER INFORMATION: primer sequence

<400> SEQUENCE: 29
```
tgaacttcca cgccatgttc                                          20

<210> SEQ ID NO 30
<211> LENGTH: 21
<212> TYPE: DNA
<213> ORGANISM: artificial sequence
<220> FEATURE:
<223> OTHER INFORMATION: primer sequence

<400> SEQUENCE: 30
tcatcgtcgc cttctcgtat g                                        21

<210> SEQ ID NO 31
<211> LENGTH: 22
<212> TYPE: DNA
<213> ORGANISM: artificial sequence
<220> FEATURE:
<223> OTHER INFORMATION: primer sequence

<400> SEQUENCE: 31
cgtgaggctg gatctcaaaa ag                                       22

<210> SEQ ID NO 32
<211> LENGTH: 20
<212> TYPE: DNA
<213> ORGANISM: artificial sequence
<220> FEATURE:
<223> OTHER INFORMATION: primer sequence

<400> SEQUENCE: 32
ttgatcacgc cagactttgc                                          20

<210> SEQ ID NO 33
<211> LENGTH: 22
<212> TYPE: DNA
<213> ORGANISM: artificial sequence
<220> FEATURE:
<223> OTHER INFORMATION: primer sequence

<400> SEQUENCE: 33
ctggtaagaa tggtgccaaa gg                                       22

<210> SEQ ID NO 34
<211> LENGTH: 20
<212> TYPE: DNA
<213> ORGANISM: artificial sequence
<220> FEATURE:
<223> OTHER INFORMATION: primer sequence

<400> SEQUENCE: 34
ttgccatctt cgcctttagc                                          20

<210> SEQ ID NO 35
<211> LENGTH: 20
<212> TYPE: DNA
<213> ORGANISM: artificial sequence
<220> FEATURE:
<223> OTHER INFORMATION: primer sequence

<400> SEQUENCE: 35
ttatgccaga aaccttcgc                                           20

<210> SEQ ID NO 36
<211> LENGTH: 21
<212> TYPE: DNA

```
<213> ORGANISM: artificial sequence
<220> FEATURE:
<223> OTHER INFORMATION: primer sequence

<400> SEQUENCE: 36
acccatagct tcagacaagg c                                              21

<210> SEQ ID NO 37
<211> LENGTH: 20
<212> TYPE: DNA
<213> ORGANISM: artificial sequence
<220> FEATURE:
<223> OTHER INFORMATION: primer sequence

<400> SEQUENCE: 37
aacccgagga cgaaaacttg                                                20

<210> SEQ ID NO 38
<211> LENGTH: 20
<212> TYPE: DNA
<213> ORGANISM: artificial sequence
<220> FEATURE:
<223> OTHER INFORMATION: primer sequence

<400> SEQUENCE: 38
acaagtcgca tgttccagac                                                20
```

ANTI-AGING COMPOSITIONS AND METHODS FOR USING SAME

CROSS REFERENCE TO RELATED APPLICATIONS

This application claims the benefit of priority to U.S. Provisional Patent Application Ser. No. 62/250,910, filed Nov. 4, 2015, which is hereby incorporated herein by reference in its entirety.

FIELD OF INVENTION

This disclosure relates to anti-aging compositions and methods for using same.

BACKGROUND

Cellular aging processes are important and have been implicated, in part, in many age-related diseases or conditions among aged people. There remains a lack of effective prevention or treatment methods for age-related diseases or disorders. In view of the increasing population of aged people, the rising cost of health care associated with their treatment, there remains a need for effective anti-aging compositions for the prevention or treatment of age-related diseases or disorders. This need and other needs are satisfied by the various aspects of the present disclosure.

SUMMARY

In accordance with the purpose(s) of the invention, as embodied and broadly described herein, the invention, in one aspect, relates to anti-aging methods using known compounds and pharmaceutical compositions comprising same.

Disclosed are methods for preventing cellular aging in a cell of a subject, the method comprising the step of providing to the cell an effective amount of at least one lithium compound or a pharmaceutically acceptable salt thereof, and an effective amount of at least one glycyrrhizie triterpenoid compound or a pharmaceutically acceptable salt thereof, thereby preventing the cell from aging.

Also disclosed are methods for preventing cellular aging activity in a subject, the method comprising the step of providing to the subject an effective amount of at least one intracellular alkalinizing agent or a pharmaceutically acceptable salt thereof, thereby preventing the cellular aging activity.

Also disclosed are methods method for the treatment of a subject, the method comprising the steps of: diagnosing the subject as having an age-related disorder or disease; and administering to the subject an effective amount of at least one lithium compound or a pharmaceutically acceptable salt thereof, and an effective amount of at least one glycyrrhizie triterpenoid compound or a pharmaceutically acceptable salt thereof.

Also disclosed are pharmaceutical and nutraceutical compositions comprising an effective amount of at least one lithium compound or a pharmaceutically acceptable salt thereof; and an effective amount of at least one glycyrrhizie triterpenoid compound or a pharmaceutically acceptable salt thereof; and a pharmaceutically acceptable carrier.

Also disclosed are kits comprising an effective amount of at least one lithium compound or a pharmaceutically acceptable salt thereof, an effective amount of at least one glycyrrhizie triterpenoid compound or a pharmaceutically acceptable salt thereof, and one or more of: a) at least one agent known to treat an age-related disorder or disease; b) instructions for treating the age-related disorder or disease; and c) instructions for administering the lithium compound and the glycyrrhizie triterpenoid compound in connection with the age-related disorder or disease.

While aspects of the present invention can be described and claimed in a particular statutory class, such as the system statutory class, this is for convenience only and one of skill in the art will understand that each aspect of the present invention can be described and claimed in any statutory class. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

BRIEF DESCRIPTION OF THE FIGURES

The patent or application file contains at least one drawing executed in color. Copies of this patent or patent application publication with color drawing(s) will be provided by the Office upon request and payment of the necessary fee. The accompanying figures, which are incorporated in and constitute a part of this specification, illustrate several aspects and together with the description serve to explain the principles of the invention.

Figure 1:
FIG. 1 show lithium and glycyrrhizic acid combination treated fibroblast samples stained for beta-galactosidase.

Additional advantages of the invention will be set forth in part in the description which follows, and in part will be obvious from the description, or can be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DETAILED DESCRIPTION

The present invention can be understood more readily by reference to the following detailed description of the invention and the Examples included therein.

Before the present compounds, compositions, articles, systems, devices, and/or methods are disclosed and described, it is to be understood that they are not limited to specific synthetic methods unless otherwise specified, or to particular reagents unless otherwise specified, as such may, of course, vary. It is also to be understood that the terminology used herein is for the purpose of describing particular aspects only and is not intended to be limiting. Although any methods and materials similar or equivalent to those described herein can be used in the practice or testing of the present invention, example methods and materials are now described.

While aspects of the present invention can be described and claimed in a particular statutory class, such as the system statutory class, this is for convenience only and one of skill in the art will understand that each aspect of the present invention can be described and claimed in any statutory class. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon. Nothing herein is to be construed as an admission that the present invention is not entitled to antedate such publication by virtue of prior invention. Further, the dates of publication provided herein may be different from the actual publication dates, which can require independent confirmation.

A. DEFINITIONS

As used in the specification and the appended claims, the singular forms "a," "an" and "the" include plural referents unless the context clearly dictates otherwise. Thus, for example, reference to "a functional group," "an alkyl," or "a residue" includes mixtures of two or more such functional groups, alkyls, or residues, and the like.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

References in the specification and concluding claims to parts by weight of a particular element or component in a composition denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent (wt. %) of a component, unless specifically stated to the contrary, is based on the total weight of the formulation or composition in which the component is included.

As used herein, the terms "optional" or "optionally" means that the subsequently described event or circumstance can or cannot occur, and that the description includes instances where said event or circumstance occurs and instances where it does not.

As used herein, the term "subject" can be a vertebrate, such as a mammal, a fish, a bird, a reptile, or an amphibian. Thus, the subject of the herein disclosed methods can be a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. In one aspect, the subject is a mammal. A patient refers to a subject afflicted with a disease or disorder. The term "patient" includes human and veterinary subjects. In some aspects of the disclosed methods, the subject has been diagnosed with a need for treatment of one or more disorders prior to the administering step. In some aspects of the disclosed methods, the subject has been diagnosed with a need for treatment of one or more age-related disorder or disease prior to the administering step. In some aspects of the disclosed method, the subject has been diagnosed with a chronic pulmonary disease prior to the administering step. In some aspects of the disclosed method, the subject been diagnosed with a chronic pulmonary disease prior to the administering step.

As used herein, the term "treatment" or "treating" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder. In various aspects, the term covers any treatment of a subject, including a mammal (e.g., a human), and includes: (i) preventing the disease from occurring in a subject that can be predisposed to the disease but has not yet been diagnosed as having it; (ii) inhibiting the disease, i.e., arresting its development; or (iii) relieving the disease, i.e., causing regression of the disease. In one aspect, the subject is a mammal such as a primate, and, in a further aspect, the subject is a human. The term "subject" also includes domesticated animals (e.g., cats, dogs, etc.), livestock (e.g., cattle, horses, pigs, sheep, goats, etc.), and laboratory animals (e.g., mouse, rabbit, rat, guinea pig, fruit fly, etc.).

As used herein, the term "prevent" or "preventing" refers to precluding, averting, obviating, forestalling, stopping, or hindering something from happening, especially by advance action. It is understood that where reduce, inhibit or prevent are used herein, unless specifically indicated otherwise, the use of the other two words is also expressly disclosed. For example, preventing age-related disease or disorder means reducing the incidences, delaying or reversing diseases or disorders that are related to or associated with aging.

As used herein, the term "diagnosed" means having been subjected to a physical examination by a person of skill, for example, a physician, and found to have a condition that can be diagnosed or treated by the compounds, compositions, or methods disclosed herein. In some aspects of the disclosed methods, the subject has been diagnosed with a need for treatment of an age-related disorder or disease prior to the administering step. As used herein, the phrase "identified to be in need of treatment for a disorder," or the like, refers to selection of a subject based upon need for treatment of the disorder. It is contemplated that the identification can, in one aspect, be performed by a person different from the person making the diagnosis. It is also contemplated, in a further aspect, that the administration can be performed by one who subsequently performed the administration.

As used herein, the term "providing" refers to any method of administering or contacting a disclosed compound or composition to a cell, target receptor, or other biological entity. preparation to a subject. Such methods are well known to those skilled in the art and include, but are not limited to, oral administration, transdermal administration, administration by inhalation, nasal administration, topical administration, intravaginal administration, ophthalmic administration, intraaural administration, intracerebral administration, rectal administration, and parenteral administration, including injectable such as intravenous administration, intra-arterial administration, intramuscular administration, and subcutaneous administration. Administration can be continuous or intermittent. In various aspects, a preparation can be administered therapeutically; that is, administered to treat an existing disease or condition. In further various aspects, a preparation can be administered prophylactically; that is, administered for prevention of a disease or condition.

As used herein, the terms "administering" and "administration" refer to any method of providing a pharmaceutical preparation to a subject. Such methods are well known to those skilled in the art and include, but are not limited to, oral administration, transdermal administration, administration by inhalation, nasal administration, topical administration, intravaginal administration, ophthalmic administration, intraaural administration, intracerebral administration, rectal administration, and parenteral administration, including injectable such as intravenous administration, intra-arterial administration, intramuscular administration, and subcutaneous administration. Administration can be continuous or intermittent. In various aspects, a preparation can be administered therapeutically; that is, administered to treat an existing disease or condition. In further various aspects, a preparation can be administered prophylactically; that is, administered for prevention of a disease or condition.

The term "contacting" as used herein refers to bringing a disclosed compound and a cell, target receptor, or other biological entity together in such a manner that the compound can affect the activity of the target (e.g., receptor, cell, etc.), either directly; i.e., by interacting with the target itself, or indirectly; i.e., by interacting with another molecule, co-factor, factor, or protein on which the activity of the target is dependent.

As used herein, the terms "effective amount" and "amount effective" refer to an amount that is sufficient to achieve the desired result or to have an effect on an undesired condition. For example, a "therapeutically effective amount" refers to an amount that is sufficient to achieve the desired therapeutic result or to have an effect on undesired symptoms, but is generally insufficient to cause adverse side effects. The specific therapeutically effective dose level for any particular patient will depend upon a variety of factors including the disorder being treated and the severity of the disorder; the specific composition employed; the age, body weight, general health, sex and diet of the patient; the time of administration; the route of administration; the rate of excretion of the specific compound employed; the duration of the treatment; drugs used in combination or coincidental with the specific compound employed and like factors well known in the medical arts. For example, it is well within the skill of the art to start doses of a compound at levels lower than those required to achieve the desired therapeutic effect and to gradually increase the dosage until the desired effect is achieved. If desired, the effective daily dose can be divided into multiple doses for purposes of administration. Consequently, single dose compositions can contain such amounts or submultiples thereof to make up the daily dose. The dosage can be adjusted by the individual physician in the event of any contraindications. Dosage can vary, and can be administered in one or more dose administrations daily, for one or several days. Guidance can be found in the literature for appropriate dosages for given classes of pharmaceutical products. In further various aspects, a preparation can be administered in a "prophylactically effective amount"; that is, an amount effective for prevention of a disease or condition.

As used herein, the terms "age-related disorder" or "age-related disease" refers to disorders or diseases in which aging is a major risk factor. In some aspects, age-related diseases or disorders can be based on disease type, and can include three main types: (1) abnormal proliferative diseases, such as cancer; (2) degenerative diseases, including neuron degenerating disease (Alzheimer's, Parkinson's, stroke), myocardial infarction, heart failure, atherosclerosis, hypertension, osteoarthritis, osteoporosis, sarcopenia, loss of bone marrow, Rheumatoid arthritis, degraded immune function, diabetes, Idiopathic pulmonary fibrosis, age-related macular degeneration; and (3) function decreasing disorders, including declines in testosterone, estrogen, growth hormone, IGF-I, reduced energy production and so on. In other aspects, age-related diseases or disorders can also be classified based on the type of cells involved, and can include two main classes: (1) in postmitotic cells: neuron degeneration (Alzheimer's, Parkinson's, stroke), sarcopenia (loss of muscle), cardiovascular diseases (heart failure, myocardial infarction); and (2) in mitotic cells: loss of bone marrow, degraded immune function, diabetes, idiopathic pulmonary fibrosis, age-related macular degeneration, rheumatoid arthritis, osteoarthritis, osteoporosis, atherosclerosis, and hypertension. In further aspects, age-related diseases or disorders associated with mitochondrial dysfunction or/and telomere dysfunction include, but are not limited to, cancer, osteoarthritis, age-related macular degeneration, idiopathic pulmonary fibrosis (IPF), Parkinson's disease, Alzheimer's disease, Huntington's disease, skin aging, cataract, multiple sclerosis, Sjogren, Rheumatoid arthritis, atherosclerosis, myocardial infarction, heart failure, hypertension, stroke, diabetes mellitus, osteoporosis, obesity, grey hair, hearing loss, and the like. In still further aspects, the present invention encompasses, but is not limited to the foregoing diseases or disorders.

As used herein, "telomere disorder" refer to a disease or disorder characterized by or exhibiting a telomere dysfunction. In further various aspects, the dysfunction is telomere shortening. In further various aspects, a telomere disorder can comprise an immune-mediated disorder, inflammatory disorder, or chronic pulmonary disorder, such as, for example, idiopathic pulmonary fibrosis.

As used herein, the term "senescence" refers to a cell cycle-arrested state in mitotic cells, which can be induced by telomere dysfunction, DNA damage, or oncogene activation. In budding yeast, senescent cells caused by telomere dysfunction are arrested at the G2/M phase of the cell cycle. In mammalian cells, senescent cells are arrested at the G0 phase, which is a non-dividing phase outside of the cell cycle. For example, senescence in fibroblasts means that cells show no increase in number under the microscope for at least 4 days after passage and exhibit β-galactosidase positive staining.

As used herein, the term "post-mitotic cells" refers to a group of cells that are in arrested state at G0, which is a non-dividing phase outside of the cell cycle, but continue to perform their main functions for the rest of the organism's life. Post-mitotic cells include neuronal cells, heart muscle cells, and muscle cells. Some cell types in mature organisms, such as parenchymal cells of the liver and kidney, enter the G0 phase semi-permanently and can only be induced to begin dividing again under very specific circumstances. In various aspects, these types of cells can also be considered as post-mitotic cells when they are in G0 phase.

As used herein, "$IC_{50}$" is intended to refer to the concentration of a substance (e.g., a compound or a drug) that is required for 50% inhibition of a biological process, or component of a process, including a protein, subunit, organelle, ribonucleoprotein, etc. In one aspect, an $IC_{50}$ can refer to the concentration of a substance that is required for 50% inhibition in vivo, as further defined elsewhere herein. In a further aspect, $IC_{50}$ refers to the half maximal (50%) inhibitory concentration (IC) of a substance.

The term "pharmaceutically acceptable" describes a material that is not biologically or otherwise undesirable, i.e., without causing an unacceptable level of undesirable biological effects or interacting in a deleterious manner.

As used herein, the term "derivative" refers to a compound having a structure derived from the structure of a parent compound (e.g., a compound disclosed herein) and whose structure is sufficiently similar to those disclosed herein and based upon that similarity, would be expected by one skilled in the art to exhibit the same or similar activities and utilities as the claimed compounds, or to induce, as a precursor, the same or similar activities and utilities as the claimed compounds. Exemplary derivatives include salts, esters, amides, salts of esters or amides, and N-oxides of a parent compound.

Compounds described herein may comprise atoms in both their natural isotopic abundance and in non-natural abundance. The disclosed compounds can be isotopically-labeled or isotopically-substituted compounds identical to those described, but for the fact that one or more atoms are replaced by an atom having an atomic mass or mass number different from the atomic mass or mass number typically found in nature. Examples of isotopes that can be incorporated into compounds of the invention include isotopes of hydrogen, carbon, nitrogen, oxygen, phosphorous, fluorine and chlorine, such as $^{2}H$, $^{3}H$, $^{13}C$, $^{14}C$, $^{15}N$, $^{18}O$, $^{17}O$, $^{35}S$, $^{18}F$ and $^{36}Cl$, respectively. Compounds further comprise prodrugs thereof, and pharmaceutically acceptable salts of said compounds or of said prodrugs which contain the aforementioned isotopes and/or other isotopes of other atoms are within the scope of this invention. Certain isotopically-labeled compounds of the present invention, for example those into which radioactive isotopes such as $^{3}H$ and $^{14}C$ are incorporated, are useful in drug and/or substrate tissue distribution assays. Tritiated, i.e., $^{3}H$, and carbon-14, i.e., $^{14}C$, isotopes are particularly preferred for their ease of preparation and detectability. Further, substitution with heavier isotopes such as deuterium, i.e., $^{2}H$, can afford certain therapeutic advantages resulting from greater metabolic stability, for example increased in vivo half-life or reduced dosage requirements and, hence, may be preferred in some circumstances. Isotopically labeled compounds of the present invention and prodrugs thereof can generally be prepared by carrying out the procedures below, by substituting a readily available isotopically labeled reagent for a non-isotopically labeled reagent.

The compounds described in the invention can be present as a solvate. In some cases, the solvent used to prepare the solvate is an aqueous solution, and the solvate is then often referred to as a hydrate. The compounds can be present as a hydrate, which can be obtained, for example, by crystallization from a solvent or from aqueous solution. In this connection, one, two, three or any arbitrary number of solvate or water molecules can combine with the compounds according to the invention to form solvates and hydrates. Unless stated to the contrary, the invention includes all such possible solvates.

The term "co-crystal" means a physical association of two or more molecules which owe their stability through non-covalent interaction. One or more components of this molecular complex provide a stable framework in the crystalline lattice. In certain instances, the guest molecules are incorporated in the crystalline lattice as anhydrates or solvates, see e.g., Almarasson, O., et. al. (2004) *The Royal Society of Chemistry*, 1889-1896. Examples of co-crystals include p-toluenesulfonic acid and benzenesulfonic acid.

It is known that chemical substances form solids which are present in different states of order which are termed polymorphic forms or modifications. The different modifications of a polymorphic substance can differ greatly in their physical properties. The compounds according to the invention can be present in different polymorphic forms, with it being possible for particular modifications to be metastable. Unless stated to the contrary, the invention includes all such possible polymorphic forms.

Certain materials, compounds, compositions, and components disclosed herein can be obtained commercially or readily synthesized using techniques generally known to those of skill in the art. For example, the starting materials and reagents used in preparing the disclosed compounds and compositions are either available from commercial suppliers such as Aldrich Chemical Co., (Milwaukee, Wis.), Acros Organics (Morris Plains, N.J.), Fisher Scientific (Pittsburgh, Pa.), or Sigma (St. Louis, Mo.) or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991); March's Advanced Organic Chemistry, (John Wiley and Sons, 4th Edition); and Larock's Comprehensive Organic Transformations (VCH Publishers Inc., 1989).

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; and the number or type of embodiments described in the specification.

It is understood that the compositions disclosed herein have certain functions. Disclosed herein are certain structural requirements for performing the disclosed functions, and it is understood that there are a variety of structures that can perform the same function that are related to the disclosed structures, and that these structures will typically achieve the same result.

B. COMPOUNDS

In one aspect, the invention relates to compounds and compositions for use as anti-aging agents for the treatment of age-related disorders or diseases. In a further aspect, the invention relates to compounds and compositions for use in the treatment of age-related diseases and age-related disorders. More specifically, in one aspect, the present invention relates to compounds and compositions for the treatment of tumorigenesis, and malignant cancer development, myocardial infarction, cerebellar infarction, stroke, Parkinson's disease, heart failure, atherosclerosis, hypertension, cataract, age-related macular degeneration, sarcopenia, osteoarthritis, osteoporosis, loss of bone marrow, multiple sclerosis, Sjogren, Rheumatoid arthritis, decreased immune function, diabetes, idiopathic pulmonary fibrosis, and neurodegenerating disease, Alzheimer's disease, Huntington's disease, and disorders caused by dysfunction in testosterone, estrogen, growth hormone, IGF-I, or energy production.

It is contemplated that each disclosed derivative can be optionally further substituted. It is also contemplated that any one or more derivative can be optionally omitted from the invention. It is understood that the disclosed compounds can be employed in the disclosed methods of using.

In one aspect, the invention relates to lithium compounds or a pharmaceutically acceptable salt thereof. In a further aspect, the lithium compound, or a pharmaceutically acceptable salt thereof is selected from lithium chloride, lithium bromide, lithium carbonate, lithium nitrate, lithium sulfate, lithium acetate, lithium lactate, lithium citrate, lithium aspartate, lithium gluconate, lithium malate, lithium ascorbate, lithium orotate, lithium succinate, and combinations thereof. In a still further aspect, the lithium compound, or a pharmaceutically acceptable salt thereof is selected from lithium chloride, lithium bromide, lithium carbonate, lithium citrate, and lithium orotate.

In one further aspect, the lithium compound, or a pharmaceutically acceptable salt thereof is lithium chloride. In a further aspect, the lithium compound, or a pharmaceutically acceptable salt thereof is lithium bromide. In a still further aspect, the lithium compound, or a pharmaceutically acceptable salt thereof is lithium carbonate. In a yet further aspect, the lithium compound, or a pharmaceutically acceptable salt thereof is lithium citrate. In an even further aspect, the lithium compound, or a pharmaceutically acceptable salt thereof is lithium orotate.

In a further aspect, the invention relates to glycyrrhizie triterpenoid compounds or a pharmaceutically acceptable salt thereof. In a still further aspect, glycyrrhizie triterpenoid compounds include compounds, such as, for example, carbenoxolone, cicloxolone, glycyrrhizin and its aglycone derivative, enoxolone, as well as, analogues and salts thereof. In a yet further aspect, glycyrrhizin refers to (3β, 20β)-20-carboxy-11-oxo-30-norolean-12-en-3-yl 2-O-β-D-glucopyranuronosyl-α-D-glucopyranosiduronic acid, and can be used interchangeably with glycyrrhizic acid and glycyrrhizinic acid. It is a compound having the structure represented by the formula:

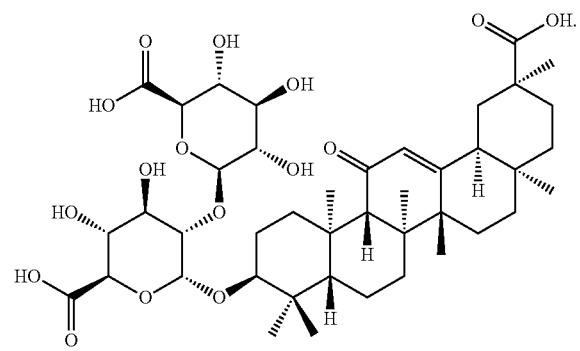

In a further aspect, enoxolone refers (2S,4aS,6aS,6bR, 8aR,10S,12aS,12bR,14bR)-10-hydroxy-2,4a,6a,6b,9,9,12a-heptamethyl-13-oxo-1,2,3,4,4a,5,6,6a,6b,7,8,8a,9,10,11,12, 12a,12b,13,14b-icosahydropicene-2-carboxylic acid, and can be used interchangeably with glycyrrhetinic acid or glycyrrhetic acid. It is commonly obtained from the hydrolysis of glycyrrhizic acid. In a still further aspect, enoxolone is a compound having the structure represented by the formula:

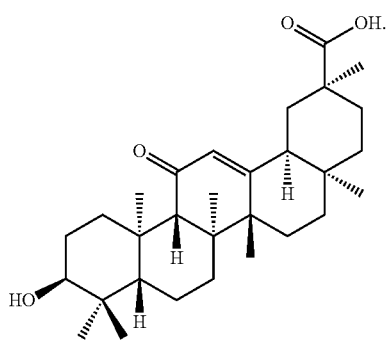

In a further aspect, glycyrrhizic acid, 20-B-carboxy-11-oxo-30-norolean-12-en-3B-yl-2-O-B-D-glucopyranuronsyl-a-D-glucopyranosiduronic acid, which can also be known as glycyrrhizin, glycyrrhizinic acid or glycyrrhetinic acid glycoside (also referred to as biosone, enoxolone, and glycyrrhetin), an extract from *glycyrrhiza*, better known as licorice, an extract of the dried rhizome and roots of *Glycyrrhiza glabra*, is an exemplary triterpene according to the present invention. In a yet further aspect, analogous triterpenes can include carbenoxolone and cicloxolone. In a still further aspect, the invention relates to glycyrrhizic acid and analogues thereof, in the form of acids, salts, esters and other derivatives. In an even further aspect, derivatives can include, such as, for example: Glycyrrhisoflavone; Benzyl glycyrrhetinate; Glycyrrhizinic acid ammonium salt; Glycyrrhizinic acid hydrolase; Glycyrrhizinic acid; Zinc glycyrrhizinate; Glycyrrhetic acid 3-0-(hydrogen sulfate); Glycyrrhetinyl stearate; Monopotassium glycyrrhetin; 3-Oxo-18-a-glycyrrhetinic acid; 11-Deoxoglycyrrhetinic acid hydrogen maleate sodium salt; 11-Deoxoglycyrrhetinic acid hydrogen maleate; 18-a-Glycyrrhizic acid diammonium salt; Monoarginine glycyrrhizinate; Potassium glycyrrhizinate; 18-a-Glycyrrhizinic acid; 18-a-Glycyrrhizic acid monosodium salt; 18-a-Glycyrrhizic acid dipotassium salt; 18-a-Glycyrrhizic acid disodium salt; 18-a-Glycyrrhizic acid monopotassium salt; Glycyrrhizinic acid mono-triethanolamine) salt; Glycyrrhizinic acid disodium salt; Trisodium glycyrrhizinate; Dipotassium glycyrrhizate; Triammonium glycyrrhizinate; Dioxoglycyrrhetinic acid; Sodium glycyrrhizate; Ammonium glycyrrhizinate; Tripotassium glycyrrhizate; Glycyrrhetinic acid nicotinate morpholine salt; Benzyl 3-0-benzyl-18-Bglycyrrhetate; 3-0-Acetylglycyrrhetaldehyde; Glycyrrhizic acid monopotassium salt; Magnesium di-3-acetyl-18-B-glycyrrhetinate; Magnesium monomethoxymono-3-acetyl-18-B-glycyrrhetinate; Dehydrocorydaline glycyrrhizate; Ruscogenin acetylglycyrrhetinate; Glycyrrhetic acid 3-0-glucuronide; Cinoxolone; crotyl glycyrrhetate; Glycyrrhizin trimethyl ester; 3-0-Acetylglycyrrhetoyl chloride; Aluminum acetylglycyrrhetate; Dipotassium glycyrrhetinate; Methyl 11-deoxo-18-aglycyrrhetate; Calcium potassium glycyrrhizinate; Glycyrrhetic acid monophosphate; B-glycyrrhetinicacid 3-acetate; 24-Hydroxyglycyrrhetic acid; 3-0-Acetyl-18-B-glycyrrhetamide; Deoxyglycyrrhetic acid; N-(18-B-Glycyrrhetyl)glycine; 3-0-Propionyl-18-B-glycyrrhetic acid; o-(18-B-Glycyrrhetamideo)benzoic acid; Glycyrrhetol; Stearyl glycyrrhetinate; Glycyrrhizic acid monosodium salt; Methyl 3-0-acetylglycyrrhetinate; Carbenoxolone sodium; Ammonium glycyrrhetinate; 3-Dehydro-18-B-glycyrrhetic acid; 3-0-Acetyl-18-B-glycyrrhetic acid; Methyl 3-0-toxylglycyrrhetate; Biogastrone; Glycyrrhetinic acid phthalate; Lauroyl glycyrrhetinate; Methyl 3-oxoglycyrrhetate; Methyl-B-glycyrrhetinate; Sodium glycyrrhetinate; Methyl glycyrrhetate; 18-a-Glycyrrhetic acid; Glycyrrhizin; 11-Deoxo-18-B-glycyrrhetic acid; Glycyrrhetic acid; and Carbenoxolone sodium.

In a further aspect, the least one glycyrrhizie triterpenoid compound is selected from glycyrrhizin, enoxolone, carbenoxolone, cicloxolone, pharmaceutically acceptable salts thereof, and combinations thereof. In a still further aspect, the least one glycyrrhizie triterpenoid is glycyrrhizin, having the structure represented by the formula:

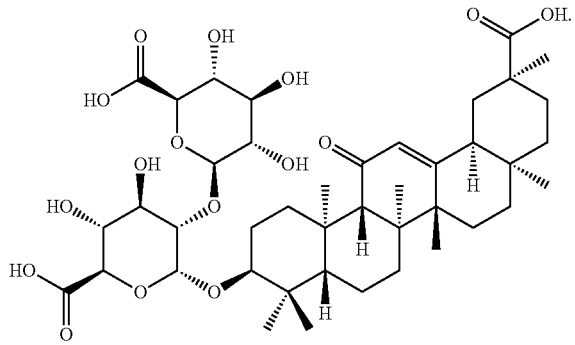

In a further aspect, the invention relates to retinoic acid compounds or a pharmaceutically acceptable salt thereof. In a still further aspect, the retinoic acid compound can comprise all-trans-retinoic acid or a cis-retinoic acid, or pharmaceutically acceptable salts thereof, and combinations thereof. In yet further aspects, the retinoic compounds include compounds, such as, for example, 7-cis-retinoic acid, 9-cis-retinoic acid, 11-cis-retinoic acid, 13-cis-retinoic acid, or pharmaceutically acceptable salts thereof, and combinations thereof.

In a further aspect, the lithium compound, or a pharmaceutically acceptable salt thereof is selected from lithium chloride, lithium bromide, lithium carbonate, lithium nitrate, lithium sulfate, lithium acetate, lithium lactate, lithium citrate, lithium aspartate, lithium gluconate, lithium malate, lithium ascorbate, lithium orotate, lithium succinate, and combinations thereof; and the glycyrrhizie triterpenoid compound is selected from glycyrrhizin, enoxolone, carbenoxolone, cicloxolone, pharmaceutically acceptable salts thereof, and combinations thereof.

In a still further aspect, the lithium compound, or a pharmaceutically acceptable salt thereof is selected from lithium chloride, lithium bromide, lithium carbonate, lithium citrate, and lithium orotate; and the least one glycyrrhizie triterpenoid compound is selected from glycyrrhizin, enoxolone, carbenoxolone, cicloxolone, pharmaceutically acceptable salts thereof, and combinations thereof.

In a yet further aspect, the lithium compound, or a pharmaceutically acceptable salt thereof is selected from lithium chloride, lithium bromide, lithium carbonate, lithium nitrate, lithium sulfate, lithium acetate, lithium lactate, lithium citrate, lithium aspartate, lithium gluconate, lithium malate, lithium ascorbate, lithium orotate, lithium succinate, and combinations thereof; and the glycyrrhizie triterpenoid compound is selected from glycyrrhizin, and pharmaceutically acceptable salts thereof.

In an even further aspect, the one lithium compound, or a pharmaceutically acceptable salt thereof is selected from lithium chloride, lithium bromide, lithium carbonate, lithium citrate, and lithium orotate; and the glycyrrhizie triterpenoid compound is selected from glycyrrhizin, and pharmaceutically acceptable salts thereof.

In a further aspect, the lithium compound, or a pharmaceutically acceptable salt thereof is selected from lithium chloride, lithium bromide, lithium carbonate, lithium citrate, and lithium orotate; and the glycyrrhizie triterpenoid compound is selected from glycyrrhizin, and pharmaceutically acceptable salts thereof.

In a further aspect, the lithium compound, or a pharmaceutically acceptable salt thereof is selected from lithium chloride, lithium bromide, lithium carbonate, lithium citrate, and lithium orotate; the glycyrrhizie triterpenoid compound is selected from glycyrrhizin, and pharmaceutically acceptable salts thereof; and the retinoic acid compound or a pharmaceutically acceptable salt thereof is selected from all-trans-retinoic 7-cis-retinoic acid, 9-cis-retinoic acid, 11-cis-retinoic acid, 13-cis-retinoic acid, and pharmaceutically acceptable salts thereof.

C. METHODS FOR AGE-RELATED DISEASES AND DISORDERS

In one aspect, the invention relates to methods for preventing cellular aging in a cell of a subject, the method comprising the step of providing to the cell an effective amount of at least one lithium compound or a pharmaceutically acceptable salt thereof, and an effective amount of at least one glycyrrhizie triterpenoid compound or a pharmaceutically acceptable salt thereof, thereby preventing the cell from aging. In further aspects, the method can further comprise the step of providing to the cell an effective amount of at least one retinoic acid compound or a pharmaceutically acceptable salt thereof.

In some aspects, the cellular anti-aging activity can comprise maintaining cell replication potential; maintaining senescence, maintaining cell cycle-arrested state in post-mitotic cells, stimulating, improving, or maintaining mitochondrial function; preventing deterioration of mitochondria, preventing cell death following senescence deterioration, or a combination thereof. In other aspects, the cellular anti-aging activity can comprise cell rejuvenation or survival.

In other aspects, the cellular anti-aging activity can comprise activity against at least one component of the TOR (Target of rapamycin) pathway, IGF-I (insulin-like growth factors) receptor pathway, EGFR (epidermal growth factor receptor) pathway, or a combination thereof. In a further aspect, the cellular anti-aging activity can comprise inhibition of at least one component of the TOR (Target of rapamycin) pathway, IGF-I (insulin-like growth factors) receptor pathway, EGFR (epidermal growth factor receptor) pathway, or a combination thereof. In a still further aspect, the at least one component can comprise an enzyme or protein.

In a further aspect, the cellular anti-aging activity comprises preventing an age-related disease or disorder. In a still further aspect, the age-related disease or disorder is associated with age-related cell loss, loss of mitochondrial function, or loss of telomere function. In a still further aspect, the age-related disease or disorder can comprise an abnormal proliferative disease, a degenerative disease, or a function-decreasing disorder. In a yet further aspect, the age-related disease or disorder can comprise tumorigenesis, and malignant cancer development, myocardial infarction, cerebellar infarction, stroke, Parkinson's disease, heart failure, atherosclerosis, hypertension, cataract, age-related macular degeneration, sarcopenia, osteoarthritis, osteoporosis, loss of bone marrow, multiple sclerosis, Sjogren, Rheumatoid arthritis, decreased immune function, diabetes, idiopathic pulmonary fibrosis, a neurodegenerating disease, Alzheimer's disease, Huntington's disease, and disorders caused by dysfunction in testosterone, estrogen, growth hormone, IGF-I, or energy production.

To treat or control the cellular aging activity, the compounds and pharmaceutical compositions comprising the compounds are provided to a cell, such as a mammalian cell, e.g., a human cell. In a further aspect, providing can comprise administering or contacting the cell with the compounds or compositions. In a still further aspect, prior to providing the compounds or compositions, the cell can be identified with a need for treatment of anti-aging treatment, as described herein.

In one aspect, the lithium compound and the glycyrrhizie triterpenoid compound are used at low doses. In a further aspect, the lithium compound and the glycyrrhizie triterpenoid compound dose is from about 0.001 to about 10000 μM in serum medium. In a still further aspect, the effective amount of the lithium compound is from about 0.01 to about 100 μM in serum medium, including exemplary subranges of about 0.1 to about 10, and about 0.2 to about 1 μM. In an even further aspect, the effective amount of the glycyrrhizie triterpenoid compound is from about 0.1 to about 1000 μM in serum medium, including exemplary subranges of about 1 to about 100, and about 1 to about 50 μM.

In a further aspect, the effective amount of the lithium compound is from about 0.1 to about 10 μM in serum medium and the effective amount of the glycyrrhizie triterpenoid compound is from about 1 to about 1000 μM in serum medium. In an even further aspect, the effective amount of the lithium compound is from about 0.1 to about 1 μM in serum medium and the effective amount of the glycyrrhizie triterpenoid compound is from about 1 to about 100 μM in serum medium. In a still further aspect, the effective amount of the lithium compound is from about 0.1 to about 0.5 μM in serum medium and the effective amount of the glycyrrhizie triterpenoid compound is from about 1 to about 50 μM in serum medium. In a yet further aspect, the ratio of lithium compound to glycyrrhizie triterpenoid compound is from about 1:10 to about 1:1000.

In one aspect, the retinoic acid compound is also used at low doses. In a further aspect, the retinoic acid compound dose can be from about 0.001 to about 10000 μM in serum medium. In a still further aspect, the effective amount of the retinoic acid compound is from about 0.01 to about 100 μM in serum medium, including exemplary subranges of about 0.1 to about 10, and about 0.2 to about 1 μM. In an even further aspect, the effective amount of the retinoic acid compound is from about 0.1 to about 1000 μM in serum medium, including exemplary subranges of about 1 to about 100, and about 1 to about 50 μM.

In a further aspect, the effective amount of the retinoic acid compound is from about 0.1 to about 10 μM in serum medium and the effective amount of the glycyrrhizie triterpenoid compound is from about 1 to about 1000 μM in serum medium. In an even further aspect, the effective amount of the retinoic acid compound is from about 0.1 to about 1 µM in serum medium and the effective amount of the retinoic acid compound is from about 1 to about 100 µM in serum medium. In a still further aspect, the effective amount of the retinoic acid compound is from about 0.1 to about 0.5 µM in serum medium and the effective amount of the retinoic acid compound is from about 1 to about 50 µM in serum medium.

In various aspects, it has been surprising discovered that the combination of the lithium compound and the glycyrrhizie triterpenoid compound at these low doses and ratios exhibit the disclosed novel anti-aging activity. In a further aspect, the anti-aging activity is not exhibited when the lithium compound and the glycyrrhizie triterpenoid compound are used as monotherapy. In a still further aspect, the synergistic anti-aging activity of the lithium compound and the glycyrrhizie triterpenoid compound is not present at higher doses.

In another aspect, the invention also relates to methods for preventing cellular aging activity in a subject, the method comprising the step of providing to the subject an effective amount of at least one intracellular alkalinizing agent or a pharmaceutically acceptable salt thereof, thereby preventing the cellular aging activity.

In a further aspect, the intracellular alkalization action comprises direct competition with Na+ on a sodium-hydrogen exchanger, increased expression or number of sodium-hydrogen exchangers, intracellular Na+ retention; increasing membrane permeability for Na+, increased Na+ reabsorption; increased secretion of H+, decreased accumulation of acid products of metabolism; or a combination thereof. In a still further aspect, the method can further comprise providing to the cell an effective amount of at least one agent for improving telomere function or a pharmaceutically acceptable salt thereof.

In a yet further aspect, the step of providing to the subject comprises providing to the subject an effective amount of at least one lithium compound or a pharmaceutically acceptable salt thereof, and an effective amount of at least one glycyrrhizie triterpenoid compound or a pharmaceutically acceptable salt thereof. In various aspects, and without wishing to be bound by a particular theory, it is believed that the lithium and glycyrrhizie triterpenoid compound increase intracellular pH, which thus exhibit anti-aging activity.

To treat or control the age-related disease or disorder, the compounds and pharmaceutical compositions comprising the compounds are administered to a subject in need thereof, such as a vertebrate, e.g., a mammal, a fish, a bird, a reptile, or an amphibian. The subject can be a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. The subject is preferably a mammal, such as a human.

In a further aspect, the subject has been diagnosed with a need for anti-aging treatment prior to the administering step. In a still further aspect, the subject has been diagnosed with an age-related disease or disorder associated with age-related cell loss, loss of mitochondrial function, or loss of telomere function. Prior to administering the compounds or compositions, the subject can be diagnosed with a need for treatment of age-related disorder or disease, such as idiopathic pulmonary fibrosis (IPF). In a still further aspect, the subject can be identified with a need for treatment of anti-aging treatment, as described herein.

The compounds or compositions can be administered to the subject according to any method. Such methods are well known to those skilled in the art and include, but are not limited to, oral administration, transdermal administration, administration by inhalation, nasal administration, topical administration, intravaginal administration, ophthalmic administration, intraaural administration, intracerebral administration, rectal administration, sublingual administration, buccal administration and parenteral administration, including injectable such as intravenous administration, intra-arterial administration, intramuscular administration, and subcutaneous administration. Administration can be continuous or intermittent. A preparation can be administered therapeutically; that is, administered to treat an existing disease or condition. A preparation can also be administered prophylactically; that is, administered for prevention of a disease or condition.

The effective amount or dosage of the compounds can vary within wide limits. Such a dosage is adjusted to the individual requirements in each particular case including the specific compound(s) being administered, the route of administration, the condition being treated, as well as the patient being treated. In general, in the case of oral or parenteral administration to adult humans weighing approximately 70 Kg or more, a daily dosage of about 1 mg to about 10,000 mg, preferably from about 2 mg to about 1,000 mg, should be appropriate, although the upper limit may be exceeded. The daily dosage can be administered as a single dose or in divided doses, or for parenteral administration, as a continuous infusion. Single dose compositions can contain such amounts or submultiples thereof of the compound or composition to make up the daily dose. The dosage can be adjusted by the individual physician in the event of any contraindications. Dosage can vary, and can be administered in one or more dose administrations daily, for one or several days. In some aspects, the compounds can be administered on a regimen of 1 to 4 times per day, preferably once or twice per day. This dosing regimen can be adjusted to provide the optimal therapeutic response.

In one aspect, the lithium compound and the glycyrrhizie triterpenoid compound are used at low doses in a subject. In a further aspect, the lithium compound and the glycyrrhizie triterpenoid compound dose is from about 0.1 mg to about 10,000 mg in a subject. In a still further aspect, the effective amount of the lithium compound is from about 0.1 mg to about 100 mg in a subject, including exemplary subranges of about 1 to about 50 mg, and about 2 to about 25 mg. In an even further aspect, the effective amount of the glycyrrhizie triterpenoid compound is from about 1 to about 1,000 mg in a subject, including exemplary subranges of about 1 to about 100 mg, and about 1 to about 50 mg.

In a further aspect, the effective amount of the lithium compound is from about 0.1 mg to about 100 mg and the effective amount of the glycyrrhizie triterpenoid compound is from about 1 to about 1000 mg in a subject. In an even further aspect, the effective amount of the lithium compound is from about 1 mg to about 50 mg and the effective amount of the glycyrrhizie triterpenoid compound is from about 1 to about 100 mg. In a still further aspect, the effective amount of the lithium compound is from about 1 to about 25 mg and the effective amount of the glycyrrhizie triterpenoid compound is from about 1 to about 50 mg. In a yet further aspect, the ratio of lithium compound to glycyrrhizie triterpenoid compound is from about 1:10 to about 1:1000.

In a further aspect, the retinoic acid compound is also used at low doses in a subject. In a further aspect, the retinoic acid compound dose is from about 0.1 mg to about 10,000 mg in a subject. In a still further aspect, the effective amount of the retinoic acid compound is from about 0.1 mg to about 100 mg in a subject, including exemplary subranges of about 1 to about 50 mg, and about 2 to about 25 mg. In an even further aspect, the effective amount of the retinoic acid compound is from about 1 to about 1,000 mg in a subject, including exemplary subranges of about 1 to about 100 mg, and about 1 to about 50 mg.

In determining the effective dose or dosage of the pharmaceutical composition of the invention, a response to a prophylactic and/or treatment method of the invention can, for example, also be measured by determining the physiological effects of the treatment or medication, such as the decrease or lack of disease symptoms following administration of the treatment or pharmacological agent. Other assays will be known to one of ordinary skill in the art and can be employed for measuring the level of the response. For example, the diagnostic methods that are used to ascertain the likelihood that a subject has an age-related disorder or disease can be used to ascertain the level of response to a prophylactic and/or treatment method of the invention. The amount of a treatment may be varied for example by increasing or decreasing the amount of a therapeutic composition, by changing the therapeutic composition administered, by changing the route of administration, by changing the dosage timing and so on. The effective amount will vary with the particular condition being treated, the age and physical condition of the subject being treated, the severity of the condition, the duration of the treatment, the nature of the concurrent therapy (if any), the specific route of administration, and the like factors within the knowledge and expertise of the health practitioner. For example, an effective amount can depend upon the degree to which an individual has abnormal levels and/or activity of a pathway associated protein or pathway associated protein complex.

The factors involved in determining an effective amount are well known to those of ordinary skill in the art and can be addressed with no more than routine experimentation. It is generally preferred that a maximum dose of the pharmacological agents of the invention (alone or in combination with other therapeutic agents) be used, that is, the highest safe dose according to sound medical judgment. It will be understood by those of ordinary skill in the art however, that a patient may insist upon a lower dose or tolerable dose for medical reasons, psychological reasons or for virtually any other reasons.

In some aspects, the effective amount is a therapeutically effective amount. In other aspects, the effective amount is a prophylactically effective amount. In further aspects, the subject is a mammal. In still further aspects, the mammal is a human.

In a further aspect, the method further comprises the step of identifying a subject in need of anti-aging treatment. In a still further aspect, the subject in need of anti-aging treatment comprises having at least one risk factor for developing an age-related disease or disorder. In a yet further aspect, the age-related disease or disorder is associated with age-related cell loss, loss of mitochondrial function, or loss of telomere function. In an even further aspect, the age-related disease or disorder comprises an abnormal proliferative disease, a degenerative disease, or a function-decreasing disorder. In an even further aspect, the age-related disease or disorder is selected from tumorigenesis, malignant cancer development, myocardial infarction, cerebellar infarction, stroke, Parkinson's disease, heart failure, atherosclerosis, hypertension, cataract, age-related macular degeneration, sarcopenia, osteoarthritis, osteoporosis, loss of bone marrow, multiple sclerosis, Sjogren, Rheumatoid arthritis, decreased immune function, diabetes, idiopathic pulmonary fibrosis, a neurodegenerating disease, Alzheimer's disease, Huntington's disease, and disorders caused by dysfunction in testosterone, estrogen, growth hormone, IGF-I, or energy production.

In another aspect, the invention also relates to a method for the treatment of a subject, the method comprising the steps of: diagnosing the subject as having an age-related disorder or disease; and administering to the subject an effective amount of at least one lithium compound or a pharmaceutically acceptable salt thereof, and an effective amount of at least one glycyrrhizie triterpenoid compound or a pharmaceutically acceptable salt thereof.

In another aspect, a method of diagnosis comprises performing an experiment upon the subject and identifying a level of a biological marker. In a further aspect diagnosing comprises determining, in a patient, levels of a marker (e.g., gene expression) indicative of a state of the patient, the state being predictive as to whether the patient will manifest reduced symptoms in response to a treatment.

In a further aspect, the biological marker is a marker for an age-related disease or disorder. In a still further aspect, the subject is a biological sample. In a still further aspect, the biological sample is selected from a cell, blood, saliva, urine, tissue, or phlegm.

In one aspect, diagnosis of an age-related disorder or disease comprises a medical history. In a further aspect, the diagnosis comprises comparing the findings of the medical history with the diagnostic standards. In a still further aspect, the diagnosis comprises finding of at least one risk factor for developing an age-related disease or disorder. In a yet further aspect, the age-related disease or disorder is associated with age-related cell loss, loss of mitochondrial function, or loss of telomere function. In an even further aspect, the age-related disease or disorder comprises an abnormal proliferative disease, a degenerative disease, or a function-decreasing disorder.

D. ANTI-AGING COMPOSITIONS

In one aspect, the invention relates to compositions comprising an effective amount of at least one lithium compound or a pharmaceutically acceptable salt thereof; and an effective amount of at least one glycyrrhizie triterpenoid compound or a pharmaceutically acceptable salt thereof. In further aspects, the compositions can comprise an effective amount of at least one retinoic acid compound or a pharmaceutically acceptable salt thereof. In some aspects, the composition can comprise pharmaceutical compositions. In other aspects, the composition can comprise nutraceutical compositions.

The compounds have anti-aging activity, and generally have $IC_{50}$ values ranging from about 0.01 micromolar to about 100 millimolar. $IC_{50}$ refers to the concentration of the compound that is required for 50% antagonism or inhibition of the target in vitro. $IC_{50}$ also refers to the concentration of a substance that is required for 50% antagonism or inhibition of the target in vivo. The activity of the compounds, including $IC_{50}$ is determined according to the procedures discussed below in the Examples section.

Pharmaceutically acceptable salts of the compounds are conventional acid-addition salts or base-addition salts that retain the biological effectiveness and properties of the compounds and are formed from suitable non-toxic organic or inorganic acids or organic or inorganic bases. Exemplary acid-addition salts include those derived from inorganic acids such as hydrochloric acid, hydrobromic acid, hydroiodic acid, sulfuric acid, sulfamic acid, phosphoric acid and nitric acid, and those derived from organic acids such as p-toluenesulfonic acid, salicylic acid, methanesulfonic acid, oxalic acid, succinic acid, citric acid, malic acid, lactic acid, fumaric acid, and the like. Example base-addition salts include those derived from ammonium, potassium, sodium and, quaternary ammonium hydroxides, such as for example, tetramethylammonium hydroxide. Chemical modification of a pharmaceutical compound into a salt is a known technique to obtain improved physical and chemical stability, hygroscopicity, flowability and solubility of compounds. See, e.g., Ansel, H. et. al., Pharmaceutical Dosage Forms and Drug Delivery Systems (6th Ed. 1995) at pp. 196 and 1456-1457.

The pharmaceutical and nutraceutical compositions comprise the compounds in a pharmaceutically acceptable carrier. A pharmaceutically acceptable carrier refers to sterile aqueous or nonaqueous solutions, dispersions, suspensions or emulsions, as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), carboxymethylcellulose and suitable mixtures thereof, vegetable oils (such as olive oil) and injectable organic esters such as ethyl oleate. The compounds can be formulated with pharmaceutically acceptable carriers or diluents as well as any other known adjuvants and excipients in accordance with conventional techniques such as those disclosed in Remington: The Science and Practice of Pharmacy, 19th Edition, Gennaro, Ed., Mack Publishing Co., Easton, Pa., 1995.

In various aspects, the disclosed pharmaceutical and nutraceutical compositions comprise the disclosed compounds (including pharmaceutically acceptable salt(s) thereof) as an active ingredient, a pharmaceutically acceptable carrier, and, optionally, other therapeutic ingredients or adjuvants. The instant compositions include those suitable for oral, rectal, topical, and parenteral (including subcutaneous, intramuscular, and intravenous) administration, although the most suitable route in any given case will depend on the particular host, and nature and severity of the conditions for which the active ingredient is being administered. The compositions can be conveniently presented in unit dosage form and prepared by any of the methods well known in the art of pharmacy.

Pharmaceutical compositions of the present invention suitable for parenteral administration can be prepared as solutions or suspensions of the active compounds in water. A suitable surfactant can be included such as, for example, hydroxypropylcellulose. Dispersions can also be prepared in glycerol, liquid polyethylene glycols, and mixtures thereof in oils. Further, a preservative can be included to prevent the detrimental growth of microorganisms.

Pharmaceutical compositions of the present invention suitable for injectable use include sterile aqueous solutions or dispersions. Furthermore, the compositions can be in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage; thus, preferably should be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), vegetable oils, and suitable mixtures thereof.

Pharmaceutical and nutraceutical compositions of the present invention can be in a form suitable for topical use such as, for example, an aerosol, cream, ointment, lotion, dusting powder, mouth washes, gargles, and the like. Further, the compositions can be in a form suitable for use in transdermal devices. These formulations can be prepared, utilizing a compound of the invention, or pharmaceutically acceptable salts thereof, via conventional processing methods. As an example, a cream or ointment is prepared by mixing hydrophilic material and water, together with about 5 wt % to about 10 wt % of the compound, to produce a cream or ointment having a desired consistency.

Pharmaceutical and nutraceutical compositions of this invention can be in a form suitable for rectal administration wherein the carrier is a solid. It is preferable that the mixture forms unit dose suppositories. Suitable carriers include cocoa butter and other materials commonly used in the art. The suppositories can be conveniently formed by first admixing the composition with the softened or melted carrier(s) followed by chilling and shaping in molds.

In various aspects, the pharmaceutical and nutraceutical compositions of this invention can include a pharmaceutically acceptable carrier and a compound or a pharmaceutically acceptable salt of the compounds of the invention. The compounds of the invention, or pharmaceutically acceptable salts thereof, can also be included in pharmaceutical and nutraceutical compositions in combination with one or more other therapeutically active compounds.

The pharmaceutical carrier employed can be, for example, a solid, liquid, or gas. Examples of solid carriers include lactose, terra alba, sucrose, talc, gelatin, agar, pectin, acacia, magnesium stearate, and stearic acid. Examples of liquid carriers are sugar syrup, peanut oil, olive oil, and water. Examples of gaseous carriers include carbon dioxide and nitrogen.

In preparing the compositions for oral dosage form, any convenient pharmaceutical media can be employed. For example, water, glycols, oils, alcohols, flavoring agents, preservatives, coloring agents and the like can be used to form oral liquid preparations such as suspensions, elixirs and solutions; while carriers such as starches, sugars, microcrystalline cellulose, diluents, granulating agents, lubricants, binders, disintegrating agents, and the like can be used to form oral solid preparations such as powders, capsules and tablets. Because of their ease of administration, tablets and capsules are the preferred oral dosage units whereby solid pharmaceutical carriers are employed. Optionally, tablets can be coated by standard aqueous or nonaqueous techniques A tablet containing the composition of this invention can be prepared by compression or molding, optionally with one or more accessory ingredients or adjuvants. Compressed tablets can be prepared by compressing, in a suitable machine, the active ingredient in a free-flowing form such as powder or granules, optionally mixed with a binder, lubricant, inert diluent, surface active or dispersing agent. Molded tablets can be made by molding in a suitable machine, a mixture of the powdered compound moistened with an inert liquid diluent.

In addition to the aforementioned carrier ingredients, the pharmaceutical formulations described above can include, as appropriate, one or more additional carrier ingredients such as diluents, buffers, flavoring agents, binders, surface-active agents, thickeners, lubricants, preservatives (including anti-oxidants) and the like. Furthermore, other adjuvants can be included to render the formulation isotonic with the blood of the intended recipient. Compositions containing a compound of the invention, and/or pharmaceutically acceptable salts thereof, can also be prepared in powder or liquid concentrate form.

In a further aspect, the effective amount is a therapeutically effective amount. In a still further aspect, the effective amount is a prophylactically effective amount.

In a further aspect, the composition is formulated for parenteral administration. In a still further aspect, the composition is formulated for inhalation. In yet a further aspect, the composition is formulated for oral administration. In an even further aspect, the composition is formulated for topical administration.

It is understood that the disclosed compositions can be prepared from the disclosed compounds. It is also understood that the disclosed compositions can be employed in the disclosed methods of using.

E. KITS

In one aspect, the invention relates to a kit comprising an effective amount of at least one lithium compound or a pharmaceutically acceptable salt thereof, an effective amount of at least one glycyrrhizie triterpenoid compound or a pharmaceutically acceptable salt thereof, and one or more of: a) at least one agent known to treat an age-related disorder or disease; b) instructions for treating the age-related disorder or disease; and c) instructions for administering the lithium compound and the glycyrrhizie triterpenoid compound in connection with the age-related disorder or disease. In a further aspect, the kit can comprise an effective amount of at least one retinoic acid compound or a pharmaceutically acceptable salt thereof, and instructions for administering the retinoic acid compound in connection with the age-related disorder or disease.

The kits can also comprise compounds co-packaged, co-formulated, and/or co-delivered with other components. For example, a drug manufacturer, a drug reseller, a physician, a compounding shop, or a pharmacist can provide a kit comprising a disclosed compound and another component for delivery to a patient.

In a further aspect, the age-related disorder or disease is associated with age-related cell loss, loss of mitochondrial function, or loss of telomere function. In a still further aspect, the age-related disease or disorder comprises an abnormal proliferative disease, a degenerative disease, or a function-decreasing disorder. In a yet further aspect, the age-related disease or disorder is selected from tumorigenesis, malignant cancer development, myocardial infarction, cerebellar infarction, stroke, Parkinson's disease, heart failure, atherosclerosis, hypertension, cataract, age-related macular degeneration, sarcopenia, osteoarthritis, osteoporosis, loss of bone marrow, multiple sclerosis, Sjogren, Rheumatoid arthritis, decreased immune function, diabetes, idiopathic pulmonary fibrosis, a neurodegenerating disease, Alzheimer's disease, Huntington's disease, and disorders caused by dysfunction in testosterone, estrogen, growth hormone, IGF-I, or energy production.

In a further aspect, the compounds and the at least one agent are co-packaged. In a still further aspect, the compounds and the at least one agent are co-formulated. In a yet further aspect, each dose of the lithium compound and the glycyrrhizie triterpenoid compound are co-packaged. In an even further aspect, each dose of the lithium compound, the glycyrrhizie triterpenoid compound, and the at least one agent are co-formulated. In a still further aspect, each dose of the lithium compound and the at least one agent are co-formulated. In a yet further aspect, each dose of the glycyrrhizie triterpenoid compound and the at least one agent are co-packaged.

In a further aspect, plurality of dosage forms, the plurality comprising one or more doses; wherein each dose comprises an effective amount of the lithium compound and the glycyrrhizie triterpenoid compound. In a still further aspect, each dose comprises an effective amount of the lithium compound, the glycyrrhizie triterpenoid compound, and the at least one agent.

In a further aspect, each dose of the lithium compound and the glycyrrhizie triterpenoid compound are administered sequentially. In a still further aspect, each dose of the lithium compound and the glycyrrhizie triterpenoid compound are administered simultaneously. In a yet further aspect, each dose of the lithium compound and the at least one agent are administered sequentially. In an even further aspect, each dose of the glycyrrhizie triterpenoid compound and the at least one agent are administered simultaneously. In a still further aspect, each dose of the lithium compound, the glycyrrhizie triterpenoid compound, and the at least one agent are administered sequentially. In a yet further aspect, each dose of the lithium compound, the glycyrrhizie triterpenoid compound, and the at least one agent are administered simultaneously.

In a still further aspect, the effective amount is a therapeutically effective amount. In yet a further aspect, the effective amount is a prophylactically effective amount.

In a further aspect, the dosage forms are formulated for oral administration, inhalation, topical administration, and/or parenteral administration. In a still further aspect, the dosage form for the compounds is formulated for oral administration. In yet a further aspect, the dosage form for the compound is formulated for oral administration and the dosage form for the at least one agent is formulated for oral administration.

In a further aspect, the agent known to treat an age-related disorder or disease can comprise nutritional supplements, anti-inflammatory medicines (e.g., NSAIDS) antiplatelet medicines (e.g., clopidogrel, aspirin), anticoagulants (e.g., warfarin, heparin), lipid lowering medicines (e.g., statins, niacin), anti-hypertensive medicines (e.g., angiotensin-converting enzyme (ACE) inhibitors, angiotensin II receptor blockers (ARBs), beta-blockers, diuretics, and calcium channel blockers (CCBs)), anti-diabetic medicines (e.g., metformin), chemotherapeutic agents, or a combination thereof. In a still further aspect, the nutritional supplement can comprise vitamins, minerals, antioxidants, amino acids, fatty acid complex, digestive enzymes, or a combination thereof.

In a further aspect, the agent can comprise a retinoic acid compound or a pharmaceutically acceptable salt thereof. In a still further aspect, the agent can comprise all-trans-retinoic acid or a cis-retinoic acid, or pharmaceutically acceptable salts thereof, and combinations thereof. In yet further aspects, the agent is selected from all-trans-retinoic acid, 7-cis-retinoic acid, 9-cis-retinoic acid, 11-cis-retinoic acid, 13-cis-retinoic acid, or pharmaceutically acceptable salts thereof, and combinations thereof.

It is understood that the disclosed kits can be prepared from the disclosed compounds, products, and pharmaceutical compositions. It is also understood that the disclosed kits can be employed in connection with the disclosed methods of using.

The disclosed compositions and methods include at least the following aspects:

Aspect 1: A method for preventing cellular aging in a cell of a subject, the method comprising the step of providing to the cell an effective amount of at least one lithium compound or a pharmaceutically acceptable salt thereof, and an effective amount of at least one glycyrrhizie triterpenoid compound or a pharmaceutically acceptable salt thereof, thereby preventing the cell from aging.

Aspect 2: The method of aspect 1, wherein the least one lithium compound, or a pharmaceutically acceptable salt thereof is selected from lithium chloride, lithium bromide, lithium carbonate, lithium nitrate, lithium sulfate, lithium acetate, lithium lactate, lithium citrate, lithium aspartate, lithium gluconate, lithium malate, lithium ascorbate, lithium orotate, lithium succinate, and combinations thereof.

Aspect 3: The method of aspects 1 or 2, wherein the least one lithium compound, or a pharmaceutically acceptable salt thereof is selected from lithium chloride, lithium bromide, lithium carbonate, lithium citrate, and lithium orotate.

Aspect 4: The method of any preceding aspect, wherein the least one glycyrrhizie triterpenoid compound is selected from glycyrrhizin, enoxolone, carbenoxolone, cicloxolone, pharmaceutically acceptable salts thereof, and combinations thereof.

Aspect 5: The method of any preceding aspect, wherein the least one glycyrrhizie triterpenoid is glycyrrhizin, having the structure represented by the formula:

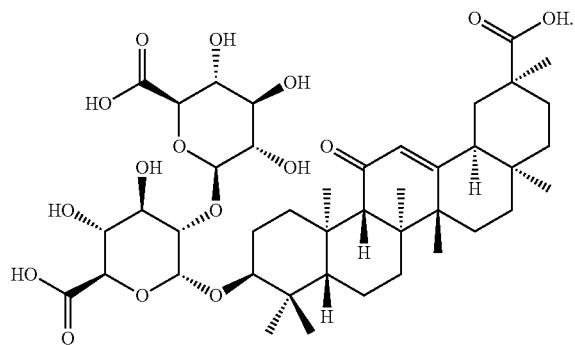

Aspect 6: The method of any preceding aspect, wherein the least one lithium compound, or a pharmaceutically acceptable salt thereof is selected from lithium chloride, lithium bromide, lithium carbonate, lithium nitrate, lithium sulfate, lithium acetate, lithium lactate, lithium citrate, lithium aspartate, lithium gluconate, lithium malate, lithium ascorbate, lithium orotate, lithium succinate, and combinations thereof; and wherein the least one glycyrrhizie triterpenoid compound is selected from glycyrrhizin, enoxolone, carbenoxolone, cicloxolone, pharmaceutically acceptable salts thereof, and combinations thereof.

Aspect 7: The method of any preceding aspect, wherein the least one lithium compound, or a pharmaceutically acceptable salt thereof is selected from lithium chloride, lithium bromide, lithium carbonate, lithium citrate, and lithium orotate; and wherein the least one glycyrrhizie triterpenoid compound is selected from glycyrrhizin, enoxolone, carbenoxolone, cicloxolone, pharmaceutically acceptable salts thereof, and combinations thereof.

Aspect 8: The method of any preceding aspect, wherein the least one lithium compound, or a pharmaceutically acceptable salt thereof is selected from lithium chloride, lithium bromide, lithium carbonate, lithium nitrate, lithium sulfate, lithium acetate, lithium lactate, lithium citrate, lithium aspartate, lithium gluconate, lithium malate, lithium ascorbate, lithium orotate, lithium succinate, and combinations thereof; and wherein the least one glycyrrhizie triterpenoid compound is selected from glycyrrhizin, and pharmaceutically acceptable salts thereof.

Aspect 9: The method of any preceding aspect, wherein the least one lithium compound, or a pharmaceutically acceptable salt thereof is selected from lithium chloride, lithium bromide, lithium carbonate, lithium citrate, and lithium orotate; and wherein the least one glycyrrhizie triterpenoid compound is selected from glycyrrhizin, and pharmaceutically acceptable salts thereof.

Aspect 10: The method of any preceding aspect, wherein the least one lithium compound, or a pharmaceutically acceptable salt thereof is selected from lithium chloride, lithium bromide, lithium carbonate, lithium citrate, and lithium orotate; and wherein the least one glycyrrhizie triterpenoid compound is selected from glycyrrhizin, and pharmaceutically acceptable salts thereof.

Aspect 11: The method of any preceding aspect, wherein the least one glycyrrhizie triterpenoid compound is an extract from *glycyrrhiza* (licorice), an extract of the dried rhizome and roots of *Glycyrrhiza glabra*, or a combination thereof.

Aspect 12: The method of any preceding aspect, wherein the cellular anti-aging activity comprises: maintaining cell replication potential; maintaining senescence, maintaining cell cycle-arrested state in post-mitotic cells, stimulating, improving, or maintaining mitochondrial function; preventing deterioration of mitochondria, preventing cell death following senescence deterioration, or a combination thereof.

Aspect 13: The method of any preceding aspect, wherein the cellular anti-aging activity comprises: activity against at least one component of the TOR (Target of rapamycin) pathway, IGF-I (insulin-like growth factors) receptor pathway, EGFR (epidermal growth factor receptor) pathway, or a combination thereof.

Aspect 14: The method of any preceding aspect, wherein the cellular anti-aging activity comprises inhibition of at least one component of the TOR (Target of rapamycin) pathway, IGF-I (insulin-like growth factors) receptor pathway, EGFR (epidermal growth factor receptor) pathway, or a combination thereof.

Aspect 15: The method of any preceding aspect, wherein the at least one component comprises an enzyme or a protein.

Aspect 16: The method of any preceding aspect, wherein the cellular anti-aging activity comprises preventing an age-related disease or disorder.

Aspect 17: The method of any preceding aspect, wherein the age-related disease or disorder is associated with age-related cell loss, loss of mitochondrial function, or loss of telomere function.

Aspect 18: The method of any preceding aspect, wherein the age-related disease or disorder comprises an abnormal proliferative disease, a degenerative disease, or a function-decreasing disorder.

Aspect 19: The method of any preceding aspect, wherein the age-related disease or disorder is selected from tumorigenesis, malignant cancer development, myocardial infarction, cerebellar infarction, stroke, Parkinson's disease, heart failure, atherosclerosis, hypertension, cataract, age-related macular degeneration, sarcopenia, osteoarthritis, osteoporosis, loss of bone marrow, multiple sclerosis, Sjogren, Rheumatoid arthritis, decreased immune function, diabetes, idiopathic pulmonary fibrosis, a neurodegenerating disease, Alzheimer's disease, Huntington's disease, and disorders caused by dysfunction in testosterone, estrogen, growth hormone, IGF-I, or energy production.

Aspect 20: The method of any preceding aspect, wherein the cell is a mammalian cell.

Aspect 21: The method of aspect 20, wherein the mammalian cell is a human cell.

Aspect 22: The method of any preceding aspect, wherein the effective amount is a therapeutically effective amount.

Aspect 23: The method of any preceding aspect, wherein the effective amount is a prophylactically effective amount.

Aspect 24: The method of any preceding aspect, further comprising the step of identifying a cell in need of anti-aging treatment.

Aspect 25: The method of any preceding aspect, wherein the effective amount of the lithium compound and the glycyrrhizie triterpenoid compound are from about 0.001 to about 10000 µM in serum medium.

Aspect 26: The method of any preceding aspect, wherein the effective amount of the lithium compound is from about 0.1 to about 10 µM in serum medium and the effective amount of the glycyrrhizie triterpenoid compound is from about 1 to about 1000 µM in serum medium.

Aspect 27: The method of any preceding aspect, wherein the effective amount of the lithium compound is from about 0.1 to about 1 µM in serum medium and the effective amount of the glycyrrhizie triterpenoid compound is from about 1 to about 100 µM in serum medium.

Aspect 28: The method of any preceding aspect, wherein the ratio of lithium compound to glycyrrhizie triterpenoid compound is from about 1:10 to about 1:1000.

Aspect 29: The method of any preceding aspect, wherein the ratio of lithium compound to glycyrrhizie triterpenoid compound is from about 1:50 to about 1:250.

Aspect 30: A method for preventing cellular aging activity in a subject, the method comprising the step of providing to the subject an effective amount of at least one intracellular alkalinizing agent or a pharmaceutically acceptable salt thereof, thereby preventing the cellular aging activity.

Aspect 31: The method of aspect 30, wherein the intracellular alkalization action comprises direct competition with Na+ on a sodium-hydrogen exchanger, increased expression or number of sodium-hydrogen exchangers, intracellular Na+retention; increasing membrane permeability for Na+, increased Na+ reabsorption; increased secretion of H+, decreased accumulation of acid products of metabolism; or a combination thereof.

Aspect 32: The method of any preceding aspect, further comprising providing to the cell an effective amount of at least one agent for improving telomere function or a pharmaceutically acceptable salt thereof.

Aspect 33: The method of any preceding aspect, wherein the step of providing to the subject comprises providing to the subject an effective amount of at least one lithium compound or a pharmaceutically acceptable salt thereof, and an effective amount of at least one glycyrrhizie triterpenoid compound or a pharmaceutically acceptable salt thereof.

Aspect 34: The method of any preceding aspect, wherein the subject has been diagnosed with a need for anti-aging treatment prior to the administering step.

Aspect 35: The method of any preceding aspect, wherein the subject has been diagnosed with an age-related disease or disorder associated with age-related cell loss, loss of mitochondrial function, or loss of telomere function.

Aspect 36: The method of any preceding aspect, wherein the age-related disease or disorder comprises an abnormal proliferative disease, a degenerative disease, or a function-decreasing disorder.

Aspect 37: The method of any preceding aspect, wherein the age-related disease or disorder is selected from tumorigenesis, malignant cancer development, myocardial infarction, cerebellar infarction, stroke, Parkinson's disease, heart failure, atherosclerosis, hypertension, cataract, age-related macular degeneration, sarcopenia, osteoarthritis, osteoporosis, loss of bone marrow, multiple sclerosis, Sjogren, Rheumatoid arthritis, decreased immune function, diabetes, idiopathic pulmonary fibrosis, a neurodegenerating disease, Alzheimer's disease, Huntington's disease, and disorders caused by dysfunction in testosterone, estrogen, growth hormone, IGF-I, or energy production.

Aspect 38: The method of any preceding aspect, wherein the subject is a mammal.

Aspect 39: The method of any preceding aspect, wherein the mammal is a human.

Aspect 40: The method of any preceding aspect, wherein the effective amount is a therapeutically effective amount.

Aspect 41: The method of any preceding aspect, wherein the effective amount is a prophylactically effective amount.

Aspect 42: The method of any preceding aspect, further comprising the step of identifying a subject in need of anti-aging treatment.

Aspect 43: The method of any preceding aspect, wherein the subject in need of anti-aging treatment comprises having at least one risk factor for developing an age-related disease or disorder Aspect 44: The method of any preceding aspect, wherein the age-related disease or disorder is associated with age-related cell loss, loss of mitochondrial function, or loss of telomere function.

Aspect 45: The method of any preceding aspect, wherein the age-related disease or disorder comprises an abnormal proliferative disease, a degenerative disease, or a function-decreasing disorder.

Aspect 46: The method of any preceding aspect, wherein the age-related disease or disorder is selected from tumorigenesis, malignant cancer development, myocardial infarction, cerebellar infarction, stroke, Parkinson's disease, heart failure, atherosclerosis, hypertension, cataract, age-related macular degeneration, sarcopenia, osteoarthritis, osteoporosis, loss of bone marrow, multiple sclerosis, Sjogren, Rheumatoid arthritis, decreased immune function, diabetes, idiopathic pulmonary fibrosis, a neurodegenerating disease, Alzheimer's disease, Huntington's disease, and disorders caused by dysfunction in testosterone, estrogen, growth hormone, IGF-I, or energy production.

Aspect 47: The method of any preceding aspect, further comprising the step of providing to the cell an effective amount of at least one retinoic acid compound or a pharmaceutically acceptable salt thereof.

Aspect 48: The method of any preceding aspect, wherein the at least one retinoic acid compound is selected from all-trans-retinoic 7-cis-retinoic acid, 9-cis-retinoic acid, 11-cis-retinoic acid, and 13-cis-retinoic acid.

Aspect 49: The method of any preceding aspect, wherein the effective amount of the retinoic acid compound is from about 0.001 to about 10000 µM in serum medium.

Aspect 50: A method for the treatment of a subject, the method comprising the steps of: (a) diagnosing the subject as having an age-related disorder or disease; and (b) administering to the subject an effective amount of at least one lithium compound or a pharmaceutically acceptable salt thereof, and an effective amount of at least one glycyrrhizie triterpenoid compound or a pharmaceutically acceptable salt thereof.

Aspect 51: The method of any preceding aspect, wherein diagnosing comprises performing a physical examination upon the subject and making a finding.

Aspect 52: The method of any preceding aspect, wherein the finding comprises identifying at least one risk factor for developing an age-related disease or disorder Aspect 53: The method of any preceding aspect, wherein diagnosing comprises performing an experiment upon the subject and identifying a level of a biological marker.

Aspect 54: The method of any preceding aspect, wherein the biological marker is a marker for an age-related disease or disorder.

Aspect 55: The method of any preceding aspect, where in the subject is a biological sample.

Aspect 56: The method of any preceding aspect, where in the biological sample is selected from a cell, blood, saliva, urine, tissue, or phlegm.

Aspect 57: The method of any preceding aspect, wherein the age-related disease or disorder is associated with age-related cell loss, loss of mitochondrial function, or loss of telomere function.

Aspect 58: The method of any preceding aspect, wherein the age-related disease or disorder comprises an abnormal proliferative disease, a degenerative disease, or a function-decreasing disorder.

Aspect 59: The method of any preceding aspect, wherein the age-related disease or disorder is selected from tumorigenesis, malignant cancer development, myocardial infarction, cerebellar infarction, stroke, Parkinson's disease, heart failure, atherosclerosis, hypertension, cataract, age-related macular degeneration, sarcopenia, osteoarthritis, osteoporosis, loss of bone marrow, multiple sclerosis, Sjogren, Rheumatoid arthritis, decreased immune function, diabetes, idiopathic pulmonary fibrosis, a neurodegenerating disease, Alzheimer's disease, Huntington's disease, and disorders caused by dysfunction in testosterone, estrogen, growth hormone, IGF-I, or energy production.

Aspect 60: The method of any preceding aspect, wherein the effective amount of the lithium compound is from about 1 mg to about 50 mg and the effective amount of the glycyrrhizie triterpenoid compound is from about 1 to about 100 mg.

Aspect 61: The method of any preceding aspect, wherein the effective amount of the lithium compound is from about 1 to about 25 mg and the effective amount of the glycyrrhizie triterpenoid compound is from about 1 to about 50 mg.

Aspect 62: The method of any preceding aspect, further comprising administrating to the subject an effective amount of at least one retinoic acid compound or a pharmaceutically acceptable salt thereof.

Aspect 63: The method of any preceding aspect, wherein the effective amount of the retinoic acid compound is from about 1 to about 100 mg.

Aspect 64: A pharmaceutical composition comprising an effective amount of at least one lithium compound or a pharmaceutically acceptable salt thereof; and an effective amount of at least one glycyrrhizie triterpenoid compound or a pharmaceutically acceptable salt thereof;

Aspect 65: The composition of any preceding aspect, wherein the effective amount is a therapeutically effective amount.

Aspect 66: The composition of any preceding aspect, wherein the effective amount is a prophylactically effective amount.

Aspect 67: The composition of any preceding aspect, wherein the composition is formulated for oral administration.

Aspect 68: The composition of any preceding aspect, wherein the composition is formulated for topical administration.

Aspect 69: A nutraceutical composition comprising an effective amount of at least one lithium compound or a pharmaceutically acceptable salt thereof; and an effective amount of at least one glycyrrhizie triterpenoid compound or a pharmaceutically acceptable salt thereof.

Aspect 70: The composition of any preceding aspect, further comprising an effective amount of at least one retinoic acid compound or a pharmaceutically acceptable salt thereof.

Aspect 71: A kit comprising an effective amount of at least one lithium compound or a pharmaceutically acceptable salt thereof, an effective amount of at least one glycyrrhizie triterpenoid compound or a pharmaceutically acceptable salt thereof, and one or more of: (a) at least one agent known to treat an age-related disorder or disease; (b) instructions for treating the age-related disorder or disease; and (c) instructions for administering the lithium compound and the glycyrrhizie triterpenoid compound in connection with the age-related disorder or disease.

Aspect 72: The kit of aspect 71, wherein each dose of the lithium compound and the glycyrrhizie triterpenoid compound are co-packaged.

Aspect 73: The kit of any preceding aspect, wherein each dose of the lithium compound, the glycyrrhizie triterpenoid compound, and the at least one agent are co-formulated.

Aspect 74: The kit of any preceding aspect, wherein each dose of the lithium compound and the at least one agent are co-formulated.

Aspect 75: The kit of any preceding aspect, wherein each dose of the glycyrrhizie triterpenoid compound and the at least one agent are co-packaged.

Aspect 76: The kit of any preceding aspect, further comprising a plurality of dosage forms, the plurality comprising one or more doses; wherein each dose comprises an effective amount of the lithium compound and the glycyrrhizie triterpenoid compound.

Aspect 77: The kit of any preceding aspect, further comprising a plurality of dosage forms, the plurality comprising one or more doses; wherein each dose comprises an effective amount of the lithium compound, the glycyrrhizie triterpenoid compound, and the at least one agent.

Aspect 78: The kit of any preceding aspect, wherein the effective amount is a therapeutically effective amount.

Aspect 79: The kit of any preceding aspect, wherein the effective amount is a prophylactically effective amount.

Aspect 80: The kit of any preceding aspect, wherein each dose of the lithium compound and the glycyrrhizie triterpenoid compound are administered sequentially.

Aspect 81: The kit of any preceding aspect, wherein each dose of the lithium compound and the glycyrrhizie triterpenoid compound are administered simultaneously.

Aspect 82: The kit of any preceding aspect, wherein each dose of the lithium compound and the at least one agent are administered sequentially.

Aspect 83: The kit of any preceding aspect, wherein each dose of the glycyrrhizie triterpenoid compound and the at least one agent are administered simultaneously.

Aspect 84: The kit of any preceding aspect, wherein each dose of the lithium compound, the glycyrrhizie triterpenoid compound, and the at least one agent are administered sequentially.

Aspect 85: The kit of any preceding aspect, wherein each dose of the lithium compound, the glycyrrhizie triterpenoid compound, and the at least one agent are administered simultaneously.

Aspect 86: The kit of any preceding aspect, wherein the dosage forms are formulated for oral administration, inhalation administration, topical administration, and/or parenteral administration.

Aspect 87: The kit of any preceding aspect, wherein the age-related disorder or disease is associated with age-related cell loss, loss of mitochondrial function, or loss of telomere function.

Aspect 88: The kit of any preceding aspect, wherein the age-related disease or disorder comprises an abnormal proliferative disease, a degenerative disease, or a function-decreasing disorder.

Aspect 89: The kit of any preceding aspect, wherein the age-related disease or disorder is selected from tumorigenesis, malignant cancer development, myocardial infarction, cerebellar infarction, stroke, Parkinson's disease, heart failure, atherosclerosis, hypertension, cataract, age-related macular degeneration, sarcopenia, osteoarthritis, osteoporosis, loss of bone marrow, multiple sclerosis, Sjogren, Rheumatoid arthritis, decreased immune function, diabetes, idiopathic pulmonary fibrosis, a neurodegenerating disease, Alzheimer's disease, Huntington's disease, and disorders caused by dysfunction in testosterone, estrogen, growth hormone, IGF-I, or energy production.

Aspect 90: The kit of any preceding aspect, wherein the agent known to treat an age-related disorder or disease comprises nutritional supplements, anti-inflammatory medicines, antiplatelet medicines, anticoagulants, lipid lowering medicines, anti-hypertensive medicines, anti-diabetic medicines, chemotherapeutic agents, or a combination thereof.

Aspect 91: The kit of any preceding aspect, wherein the nutritional supplement comprises vitamins, minerals, antioxidants, amino acids, fatty acid complex, digestive enzymes, or a combination thereof.

Aspect 92: The kit of any preceding aspect, further comprising an effective amount of at least one retinoic acid compound or a pharmaceutically acceptable salt thereof, and instructions for administering the retinoic acid compound in connection with the age-related disorder or disease.

F. EXAMPLES

The following examples are put forth so as to provide those of ordinary skill in the art with a complete disclosure and description of how the compounds, compositions, articles, devices and/or methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

The Examples are provided herein to illustrate the invention, and should not be construed as limiting the invention in any way. Examples are provided herein to illustrate the invention and should not be construed as limiting the invention in any way.

1. Beta-Galactosidase Staining of Normal Human Fibroblasts

Aging-associated beta-galactosidase is widely used as a biomarker of senescence. Here we investigated senescence-associated-beta-galactosidase activity of human colon fibroblast cells by visual assessment.

In this Example, the effect of treatment with lithium and glycyrrhizic acid separately, and as a fixed combination, was evaluated on normal human colon fibroblast cell line CCD 841 CoN (CRL-1790, ATCC).

The general study methods of study were as follows:

Flasks, Thermo Scientific Nunclon Delta Surface 12.5 cm (Cat. No 136196) with EMEM complete medium were seeded with cell culture of CCD 841 CoN (CRL-1790, ATCC) and were kept at 37° C.; 5% $CO_2$ in incubator until 100% confluence was reached (2 days). Next, the flasks were kept in CO2 incubator, at 37 degrees and 5% of CO2 for additional 4 days to age the cells. After the 4 days, the EMEM medium in the flask were changed to the same medium with or without lithium carbonate and glycyrrhizic acid as explained below:

Group 1 (flasks 1-3), the medium was changed to complete EMEM medium with 0.15 µM lithium carbonate ($Li_2CO_3$; Sigma-Aldrich; Cat. No. 62472).

Group 2 (flasks 4-6), the medium was changed to complete EMEM medium with 0.25 mM glycyrrhizic acid (Glycyrrhizic acid ammonium salt from ammonium salt root (licorice); Sigma-Aldrich; Cat. No. G2137).

Group 3 (flasks 7-9), the medium was changed to complete EMEM medium with both 0.15 µM lithium carbonate and 0.25 mM glycyrrhizic acid (0.25 mM).

Group 4 (flasks 10-12, control), the medium was changed to fresh compete EMEM medium without drugs as controls.

All flasks were kept in the $CO_2$ incubator 5% $CO_2$, 37° C. for additional 48 hours for treatment. After the treatment period, all flasks were stained using senescence beta-galactosidase staining kit cell signaling (Cat. No. 9860) according to the protocol provided by the kit manual.

After staining, the flasks were examined by light microscope under 100× magnification 100× and visually evaluated and scored for visible positive beta-Galactosidase staining. FIGS. 1-4 show pictures of the staining results for each of the groups, respectively.

Figure 2:
FIG. 2 show glycyrrhizic acid monotherapy treated fibroblast samples stained for beta-galactosidase.
Figure 3:
FIG. 3 show lithium monotherapy treated fibroblast samples stained for beta-galactosidase.
Figure 4:
FIG. 4 show untreated treated fibroblast samples stained for beta-galactosidase.

As seen in FIGS. 1 and 2, the lithium carbonate treated fibroblasts and glycyrrhizic acid treated fibroblasts both stained positively for beta-galactosidase. Additionally, as seen in FIG. 4, the control (non-treated) fibroblasts also stained positively for beta-galactosidase. However, as seen in FIG. 3, fibroblasts treated using the combination of lithium carbonate and glycyrrhizic acid showed almost no positive stain for beta-galactosidase.

Digital pictures showing the staining results for each of the 12 flasks were then independently examined and scored for percentage of area of green (positive) staining based on pixels, with and without background subtraction. The data for this evaluation is provided in Tables 1 and 2.

TABLE 1

| Image # | Total original area (pixels$^2$) | Green stained area (pixels$^2$) | % green staining |
|---|---|---|---|
| 3357 | 17280000 | 141144.5 | .82 |
| 3359 | 17280000 | 212050.5 | 1.23 |
| 3362 | 17280000 | 226344.5 | 1.31 |
| 3370 | 17280000 | 1147244 | 6.64 |
| 3375 | 17280000 | 959792.5 | 5.55 |
| 3378 | 17280000 | 912119 | 5.28 |
| 3386 | 17280000 | 488604.5 | 2.83 |
| 3388 | 17280000 | 1080455 | 6.25 |

TABLE 1-continued

| Image # | Total original area (pixels²) | Green stained area (pixels²) | % green staining |
|---|---|---|---|
| 3390 | 17280000 | 905959 | 5.24 |
| 3395 | 17280000 | 1193624 | 6.91 |
| 3396 | 17280000 | 1573116 | 9.1 |
| 3397 | 17280000 | 1733095.5 | 10.03 |

TABLE 2

| Image # | Background subtraction | Selected green area | Average green area | % green stained |
|---|---|---|---|---|
| 3357 | w/o | 137278 | 141144.5 | 0.816808449 |
|  | w | 145011 |  |  |
| 3359 | w/o | 173646 | 212050.5 | 1.227144097 |
|  | w | 250455 |  |  |
| 3362 | w/o | 229830 | 226344.5 | 1.309864005 |
|  | w | 222859 |  |  |
| 3370 | w/o | 1236353 | 1147243.5 | 6.639140625 |
|  | w | 1058134 |  |  |
| 3375 | w/o | 845048 | 959792.5 | 5.554354745 |
|  | w | 1074537 |  |  |
| 3378 | w/o | 825052 | 912119 | 5.278466435 |
|  | w | 999186 |  |  |
| 3386 | w/o | 362321 | 488604.5 | 2.827572338 |
|  | w | 614888 |  |  |
| 3388 | w/o | 860394 | 1080455 | 6.252633102 |
|  | w | 1300516 |  |  |
| 3390 | w/o | 786299 | 905959 | 5.242818287 |
|  | w | 1025619 |  |  |
| 3395 | w/o | 1287179 | 1193624 | 6.907546296 |
|  | w | 1100069 |  |  |
| 3396 | w/o | 1597579 | 1573116 | 9.103680556 |
|  | w | 1548653 |  |  |
| 3397 | w/o | 1684570 | 1733095.5 | 10.02948785 |
|  | w | 1781621 |  |  |

Figure 5:
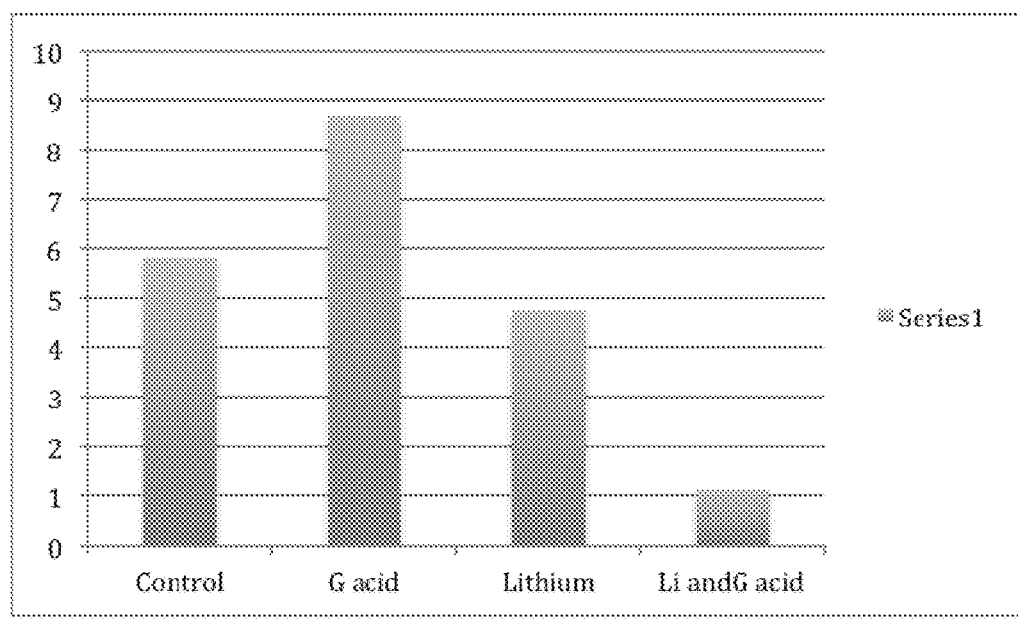
FIG. 5 show representative data pertaining to fibroblast samples.
Figure 6:
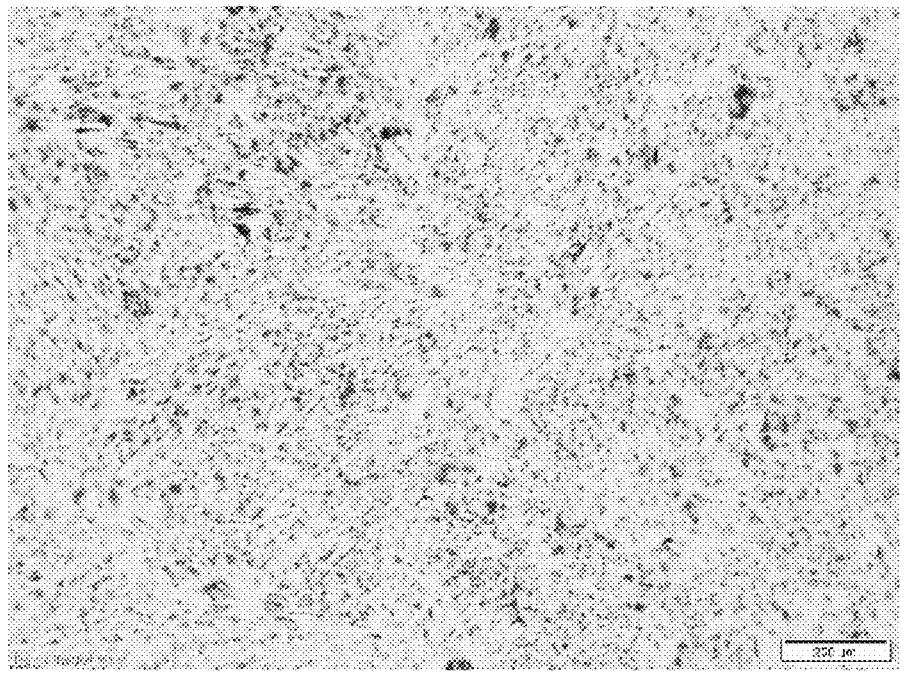
FIG. 6 show untreated treated fibroblast samples stained for beta-galactosidase.
Figure 7:
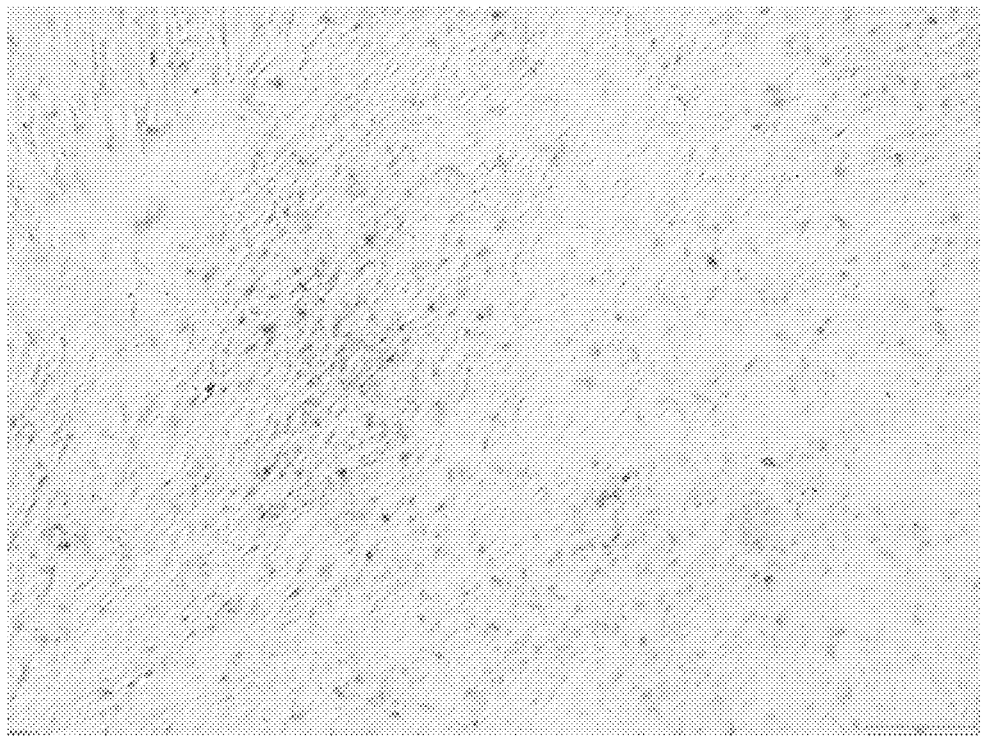
FIG. 7 show glycyrrhizic acid monotherapy treated fibroblast samples stained for beta-galactosidase.
Figure 8:
FIG. 8 show lithium monotherapy treated fibroblast samples stained for beta-galactosidase.
Figure 9:
FIG. 9 show lithium monotherapy treated fibroblast samples stained for beta-galactosidase.
Figure 10:
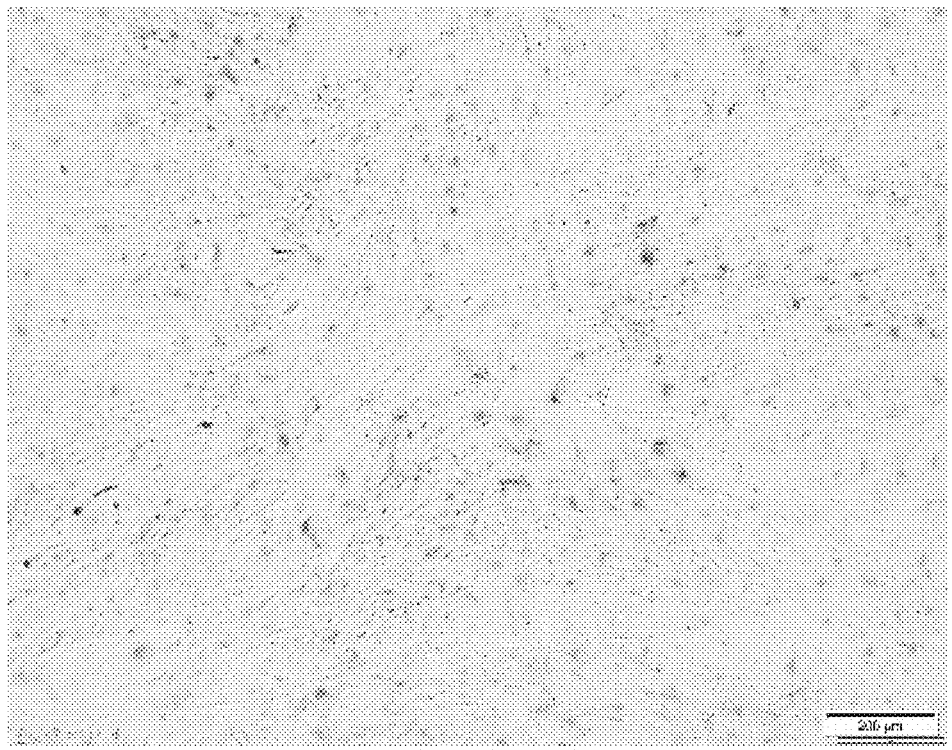
FIG. 10 show lithium monotherapy treated fibroblast samples stained for beta-galactosidase.
Figure 11:
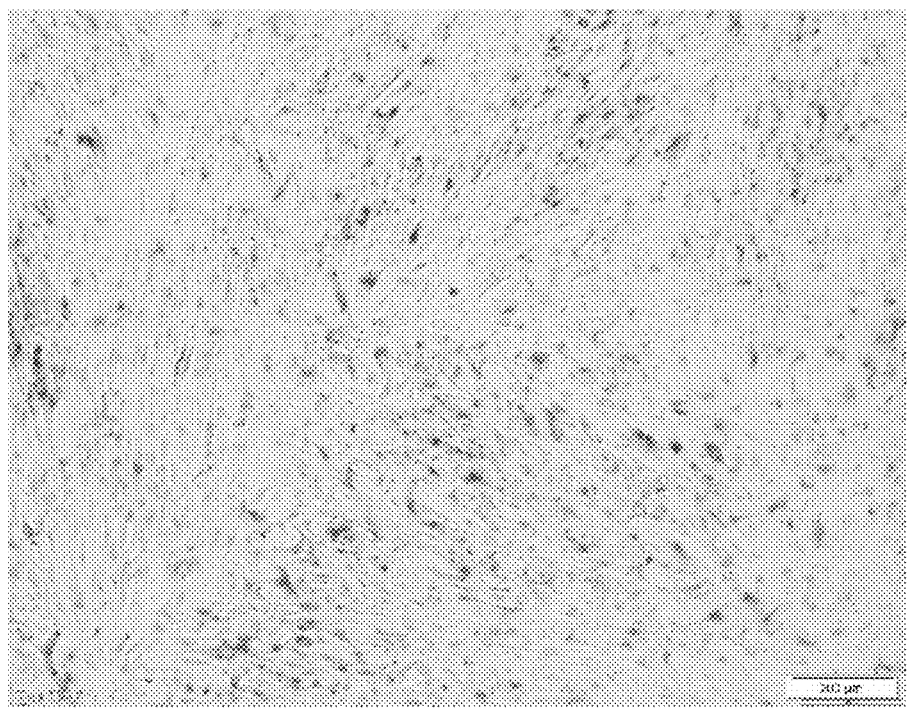
FIG. 11 show lithium monotherapy treated fibroblast samples stained for beta-galactosidase.
Figure 12:
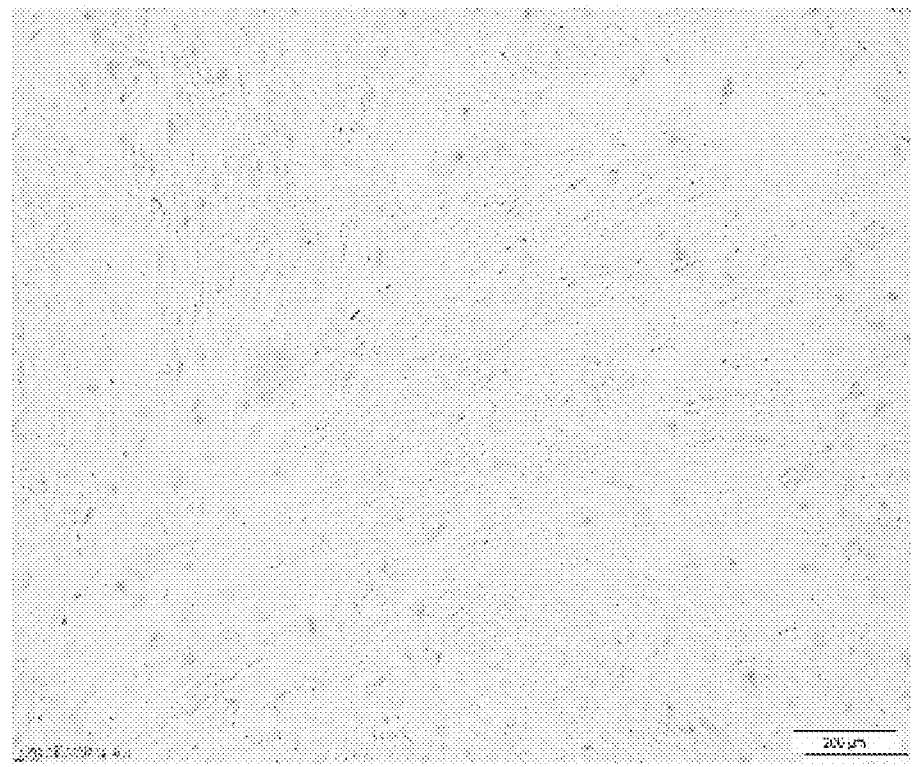
FIG. 12 show lithium and glycyrrhizic acid combination treated fibroblast samples stained for beta-galactosidase.
Figure 13:
FIG. 13 show lithium and glycyrrhizic acid combination treated fibroblast samples stained for beta-galactosidase.
Figure 14:
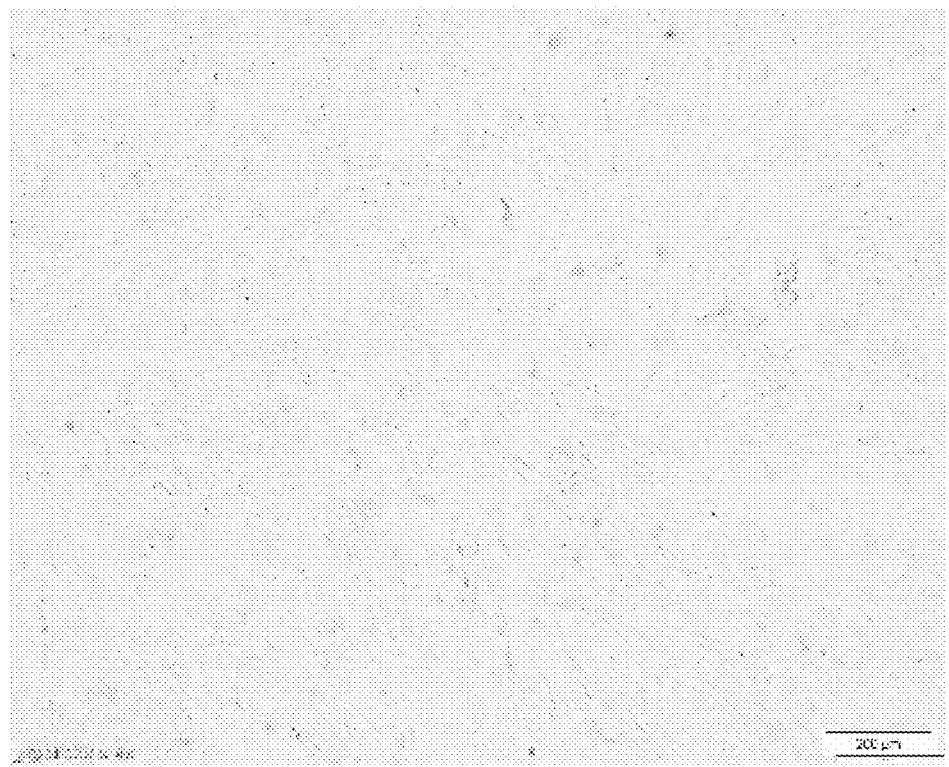
FIG. 14 show lithium and glycyrrhizic acid combination treated fibroblast samples stained for beta-galactosidase.
Figure 15:
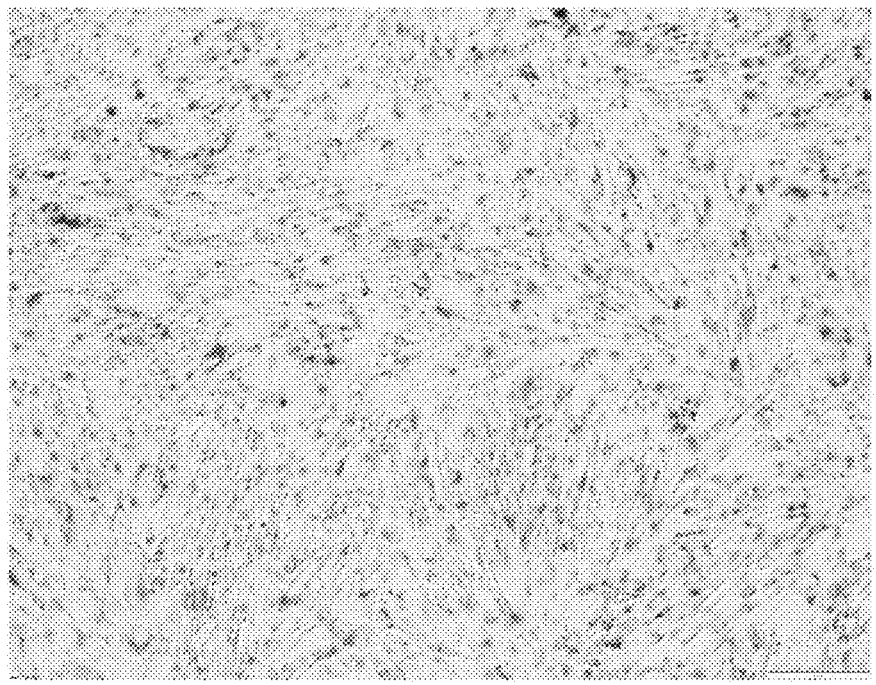
FIG. 15 show lithium and glycyrrhizic acid combination treated fibroblast samples stained for beta-galactosidase.

Table 3 shows the data from analyzed pictures for the corresponding flask and FIG. 5 shows the average % of green staining for each group. Higher values reflect more intensive green staining which corresponds to more aged cells.

TABLE 3

| Flask # | | Area | % green staining |
|---|---|---|---|
| 1 | control | 3370 | 6.64 |
| 2 | control | 3375 | 5.55 |
| 3 | control | 3378 | 5.28 |
| 4 | G acid | 3396 | 9.1 |
| 5 | G acid | 3397 | 10.03 |
| 6 | G acid | 3395 | 6.91 |
| 7 | Li | 3388 | 6.25 |
| 8 | Li | 3386 | 2.83 |
| 9 | Li | 3390 | 5.24 |
| 10 | Li and G acid | 3357 | 0.82 |
| 11 | Li and G acid | 3362 | 1.31 |
| 12 | Li and G acid | 3359 | 1.23 |

As the data show, lithium carbonate and glycyrrhizic acid alone did not appear to have significant effect on beta-galactosidase staining of the fibroblasts in comparison with non-treated controls.

However, cells treated with the combination of lithium and glycyrrhizic acid exhibited significantly less positive staining for beta-galactosidase in comparison with the lithium monotherapy and glycyrrhizic acid monotherapy. The data suggest the lithium and glycyrrhizic acid combination have a rejuvenation or anti-aging effect on the cells. Surprisingly, this rejuvenation effect is visibly observable in combination therapy, but is relevantly undetectable with monotherapy treatment.

2. Beta-Galactosidase Staining of Normal Human Fibroblasts

In this second Example, the effect of treatment with lithium and glycyrrhizic acid separately, and as a fixed combination, was further evaluated on normal human colon fibroblast cell line CCD 841 CoN (CRL-1790, ATCC).

The general study methods of study were as follows:

40 flasks Thermo Scientific Nunc Nunclon Delta Surface 12.5 cm (Cat. No. 136196) with EMEM complete medium were seeded with cell culture of CCD 841 CoN (CRL-1790, ATCC) and were kept at 37° C.; 5% $CO_2$ in incubator until 100% confluence was reached (2 days). Next, the flasks were kept in CO2 incubator, at 37 degrees and 5% of CO2 for additional 4 days to age the cells. After the 4 days, the EMEM medium in the flask were changed to the same medium with or without lithium carbonate and glycyrrhizic acid as explained below:

Group#1 contained complete EMEM medium with lithium carbonate 0.15 µM.

Group#2 contained complete EMEM medium with lithium carbonate 1.5 µM.

Group#3 contained complete EMEM medium with lithium carbonate 15 µM.

Group#4 contained complete EMEM medium with lithium carbonate 150 µM.

Group#5 contained complete EMEM medium with lithium carbonate 0.15 µM and glycyrrhizic acid 0.25 mM.

Group#6 contained complete EMEM medium with lithium carbonate 1.5 µM and glycyrrhizic acid 0.25 mM.

Group#7 contained complete EMEM medium with lithium carbonate 15 µM and glycyrrhizic acid 0.25 mM.

Group#8 contained complete EMEM medium with lithium carbonate 150 µM and glycyrrhizic acid 0.25 mM.

Group#9 contained complete EMEM medium with glycyrrhizic acid 0.25 mM.

Group#10 contained complete EMEM medium only and was used as a control.

All flasks were kept in the $CO_2$ incubator 5% CO2, 37° C. for additional 48 hours for treatment. After the treatment period, all flasks were stained using senescence beta-galactosidase staining kit cell signaling according to the protocol provided by the kit manual.

After staining, the flasks were examined by light microscope under 100× magnification 100× and visually evaluated and scored for visible positive beta-Galactosidase staining. FIGS. 6-15 show pictures of the staining results for each of the groups, respectively. As the data shows, lithium carbonate 15 µM and glycyrrhizic acid 0.25 mM combotherapy (Group #7) showed minimal green staining, which corresponds to maximum rejuvenation effect.

3. Beta-Galactosidase Staining of Normal Human Fibroblasts

In this third Example, the effect of treatment with lithium and glycyrrhizic acid separately, and as a fixed combination, was further evaluated on normal human colon fibroblast cell line CCD 841 CoN (CRL-1790, ATCC).

The general study methods of study were as follows:

Flasks Thermo Scientific Nunc Nunclon Delta Surface 12.5 cm with EMEM complete medium were seeded with cell culture of CCD 841 CoN (CRL-1790, ATCC) and were kept at 37° C.; 5% $CO_2$ in incubator until 100% confluence was reached (2 days). Next, the flasks were kept in CO2 incubator, at 37 degrees and 5% of CO2 for additional 4 days to age the cells. After the 4 days, the EMEM medium in the flask were changed to the same medium with or without lithium carbonate and/or glycyrrhizic acid as explained below:

Group#1 contained complete EMEM medium with lithium carbonate in final concentration of 0.15 µM Group#2 contained complete EMEM medium with lithium carbonate in final concentration of 1.5 µM Group#3 contained complete EMEM medium with lithium carbonate in final concentration of 15 µM Group#4 contained complete EMEM medium with lithium carbonate in final concentration of 150 µM Group#5 contained complete EMEM medium with lithium carbonate in final concentration of 0.15 µM and glycyrrhizic acid in final concentration of 0.25 mM Group#6 contained complete EMEM medium with lithium carbonate in final concentration of 1.5 µM and Glycyrrhizic acid in final concentration of 0.25 mM Group#7 contained complete EMEM medium with lithium carbonate in final concentration of 15 µM and Glycyrrhizic acid in final concentration of 0.25 mM Group#8 contained complete EMEM medium with lithium carbonate in final concentration of 150 µM and glycyrrhizic acid in final concentration of 0.25 mM Group#9 contained complete EMEM medium with glycyrrhizic acid in final concentration of 0.25 mM Group#10 contained complete EMEM medium only and was used as a control.

Figure 16:
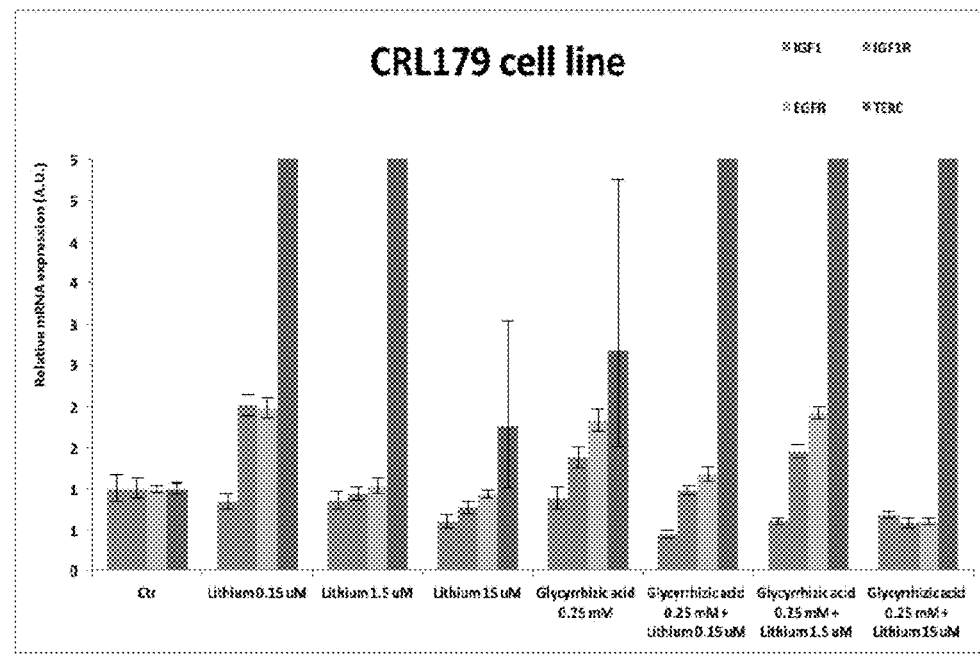
FIG. 16 show representative data pertaining gene expression profile of the fibroblast in control and treatments groups.

All flasks were kept in the $CO_2$ incubator 5% $CO_2$, 37° C. for additional 48 hours for treatment. After the treatment period, the cells were then detached from growth surface and collected in Eppendorf PCR-clean tubed in volume of 100 µL and dissolved in 0.5 ml of TRI reagent. Next, qPCR was performed in order to evaluate gene expression profile of the cell in control and treatments groups. The data from the qPCR studies are provided in FIG. 16.

As the data shows, combination therapy using glycyrrhizic acid and lithium carbonate produced diminished IGF-1, while concurrently increasing telomerase RNA component. Moreover, the specific combination of 0.25 mM glycyrrhizic acid with 15 µM lithium carbonate also appears to decrease IGF-1R and EGFR gene expression levels.

4. *C. elegans* Longevity Study

In this fourth Example, the effect of treatment with lithium and Glycyrrhizic acid separately, and as a fixed combination, was further evaluated on the wild-type N2 Bristol strain of *C. elegans*. Worm stocks were maintained on nematode growth medium (NGM) dishes containing 10 µg/mL cholesterol (Cat. No. C8667; Sigma-Aldrich, Saint Louis, Mo., USA). Dishes were seeded with OP50 *Escherichia coli* as a food source.

The general study methods of study were as follows:

Twelve polystyrene petri dishes (35 mm diameter) were prepared by filling with NGM agar containing 10 mg/ml cholesterol, and 25 µM 5-Fluoro-2'-deoxyuridine to suppress reproduction (FUDR; Cat. No. F0503; Sigma-Aldrich, Saint Louis, Mo., USA). The dishes were seeded with OP50 *Escherichia coli* as a food source. Duplicate dishes were used for each group.

The treatment drug was dissolved in deionized water, and added to the dishes for the groups as explained below:

Group#1: lithium carbonate in concentration of 0.15 µM.

Group#2: lithium carbonate in concentration of 15 µM

Group#3: lithium carbonate in concentration of 0.15 µM and Glycyrrhizic acid in concentration of 0.25 mM Group#4: lithium carbonate in concentration of 15 µM and Glycyrrhizic acid in concentration of 0.25 mM Group#5: Glycyrrhizic acid in concentration of 0.25 mM Group#6: untreated (control)

NGM-agar treatment plates containing cholesterol (10 µg/mL) and 25 µM 5-Fluoro-2'-deoxyuridine (FUDR; Cat. No. F0503; Sigma-Aldrich, Saint Louis, Mo., USA) to suppress reproduction.

Figure 17:
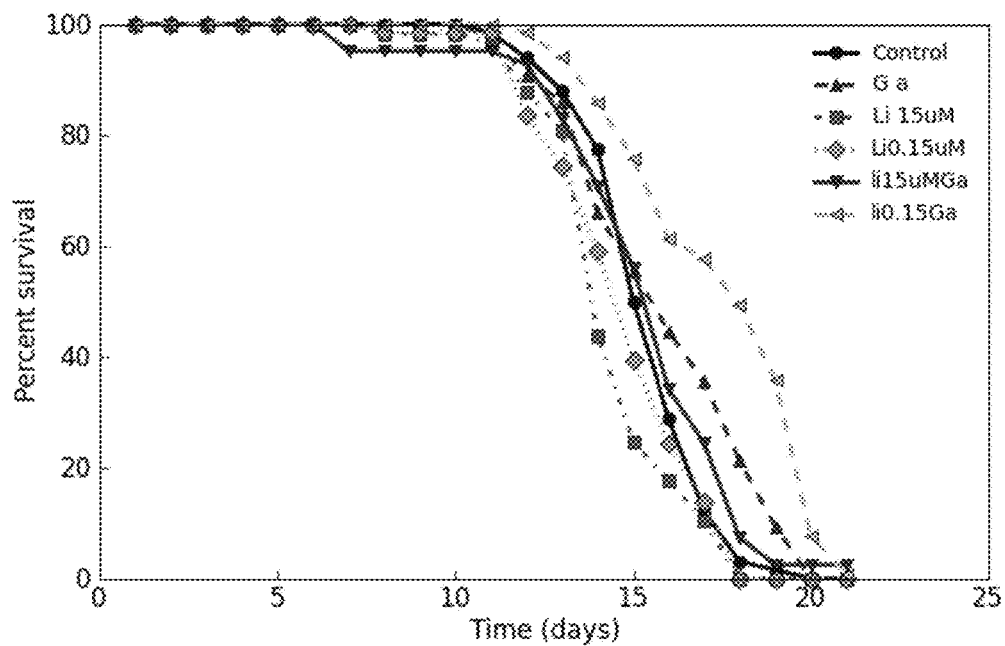
FIG. 17 show representative data pertaining survival profile of C. elegans specimens in control and treatments groups.

Treatment plates were grown overnight at room temperature (20±2° C.), and synchronized young adult worms were added to achieve a density of 19-66 worms per plate. The worms were monitored seven times a week for mortality and scored as dead when they failed to respond when prodded with a platinum pick. The data for this study is provided in Tables 4 and 5 below. The survival data for the various groups are also depicted in FIG. 17.

TABLE 4

| Name | No. of subjects | Restricted mean Days | Std. error | 95% C.I. | Age in days at % mortality 25% | 50% | 75% | 90% | 100% | 95% Median C.I. |
|---|---|---|---|---|---|---|---|---|---|---|
| Control | 66 | 15.53 | 0.21 | 15.11~15.95 | 15 | 16 | 17 | 18 | 20 | 15~15 |
| Ga | 85 | 16.06 | 0.27 | 15.53~16.59 | 14 | 16 | 18 | 19 | 20 | 15~16 |
| Li15 uM | 57 | 14.56 | 0.25 | 14.06~15.06 | 14 | 15 | 16 | 18 | 19 | 14~14 |
| Li0.15 uM | 66 | 14.88 | 0.26 | 14.37~15.39 | 13 | 15 | 16 | 18 | 19 | 14~15 |
| li15 uMGa | 41 | 15.49 | 0.43 | 14.65~16.32 | 14 | 16 | 17 | 18 | — | 15~15 |
| li0.15Ga | 132 | 17.65 | 0.22 | 17.22~18.08 | 16 | 18 | 20 | 21 | — | 17~18 |

TABLE 5

| | Statistics | | |
|---|---|---|---|
| Condition | Chi^2 | P-value | Bonferroni P-value |
| Control v.s. G a | 6.06 | 0.0139 | 0.0693 |
| Control v.s. Li 15 uM | 6.42 | 0.0113 | 0.0563 |
| Control v.s. Li0.15 uM | 4.52 | 0.0335 | 0.1673 |
| Control v.s. li15 uMGa | 1.03 | 0.3106 | 1.0000 |
| Control v.s. li0.15Ga | 46.70 | 0.0e+00 | 0.0e+00 |
| G a v.s. Control | 6.06 | 0.0139 | 0.0693 |
| G a v.s. Li 15 uM | 17.81 | 2.4e−05 | 0.0001 |
| G a v.s. Li0.15 uM | 11.51 | 0.0007 | 0.0035 |
| G a v.s. li15 uMGa | 1.51 | 0.2191 | 1.0000 |
| G a v.s. li0.15Ga | 25.35 | 4.8e−07 | 2.4e−06 |
| Li 15 uM v.s. Control | 6.42 | 0.0113 | 0.0563 |
| Li 15 uM v.s. G a | 17.81 | 2.4e−05 | 0.0001 |
| Li 15 uM v.s. Li0.15 uM | 1.05 | 0.3051 | 1.0000 |
| Li 15 uM v.s. li15 uMGa | 7.34 | 0.0067 | 0.0336 |
| Li 15 uM v.s. li0.15Ga | 72.06 | 0.0e+00 | 0.0e+00 |
| Li0.15 uM v.s. Control | 4.52 | 0.0335 | 0.1673 |
| Li0.15 uM v.s. G a | 11.51 | 0.0007 | 0.0035 |
| Li0.15 uM v.s. Li 15 uM | 1.05 | 0.3051 | 1.0000 |

TABLE 5-continued

| Condition | Statistics | | |
|---|---|---|---|
| | Chi^2 | P-value | Bonferroni P-value |
| Li0.15 uM v.s. li15 uMGa | 10.03 | 0.0015 | 0.0077 |
| Li0.15 uM v.s. li0.15Ga | 78.35 | 0.0e+00 | 0.0e+00 |
| li15 uMGa v.s. Control | 1.03 | 0.3106 | 1.0000 |
| li15 uMGa v.s. G a | 1.51 | 0.2191 | 1.0000 |
| li15 uMGa v.s. Li 15 uM | 7.34 | 0.0067 | 0.0336 |
| li15 uMGa v.s. Li0.15 uM | 10.03 | 0.0015 | 0.0077 |
| li15 uMGa v.s. li0.15Ga | 22.77 | 1.8e−06 | 9.1e−06 |
| li0.15Ga v.s. Control | 46.70 | 0.0e+00 | 0.0e+00 |
| li0.15Ga v.s. G a | 25.35 | 4.8e−07 | 2.4e−06 |
| li0.15Ga v.s. Li 15 uM | 72.06 | 0.0e+00 | 0.0e+00 |
| li0.15Ga v.s. Li0.15 uM | 78.35 | 0.0e+00 | 0.0e+00 |
| li0.15Ga v.s. li15 uMGa | 22.77 | 1.8e−06 | 9.1e−06 |

As the data show, combination therapy using 0.15 uM lithium carbonate with 0.25 mM glycyrrhizic acid significantly increased longevity and survival of the wild type *C. elegans* specimens. Surprisingly, the longevity effect is observed with specific concentrations of lithium carbonate and glycyrrhizic acid combination therapy, and is not observed at higher combination therapy concentrations or with lithium carbonate monotherapy and glycyrrhizic acid monotherapy.

5. Beta-Galactosidase Staining of Normal Human Fibroblasts

In this next Example, the effect of treatment with lithium, glycyrrhizic acid, and retinoic acid, in various combinations, was further evaluated on normal human colon fibroblast cell line CRL-1790 (ATCC).

The general study methods were as follows:

4 flasks (Thermo Scientific Nunc Nunclon Delta Surface 12.5 cm; Cat. No. 136196) with McCoy's 5A complete medium were seeded with cell culture of CRL1790 (ATCC) and were kept at 37° C.; 5% $CO_2$ in incubator until 100% confluence was reached (2 days). After reaching full confluence, in order to age cells, the flasks were kept in CO2 incubator, at 37 degrees and 5% of $CO_2$ for an additional 10 days. After 10 days of aging, the McCoy's 5A medium with 10% of FBS was changed to the same medium with or without lithium carbonate and glycyrrhizic acid and the same combination with the addition of 1 uM of retinoic acid as explained below:

Flask 1: medium was changed to complete McCoy's 5A medium with Lithium Carbonate Li2CO3 (Sigma-Aldrich; Cat. #62472) in concentration of 0.15 uM and glycyrrhzic acid (Glycyrrhizic acid ammonium salt from ammonium salt root (licorice); Sigma-Aldrich; Cat. # G2137) in concentration of 0.25 mM.

Flask 2: medium was changed to complete McCoy's 5A medium with Lithium Carbonate (0.15 uM) and Glycyrrhzic acid (0.25 mM) and retinoic acid (1 uM) (Sigma-Aldrich; Cat# R2625).

Flask 3: medium was changed to complete McCoy's 5A medium with retinoic acid (1 uM) only.

Flask 4: medium was changed to fresh McCoy's 5A compete medium only. All flasks were kept in the $CO_2$ incubator 5% CO2, 37° C. for additional 24 hours for treatment. After the treatment period, all flasks were stained using senescence beta-galactosidase staining kit cell signaling according to the protocol provided by the kit manual.

Figure 18:
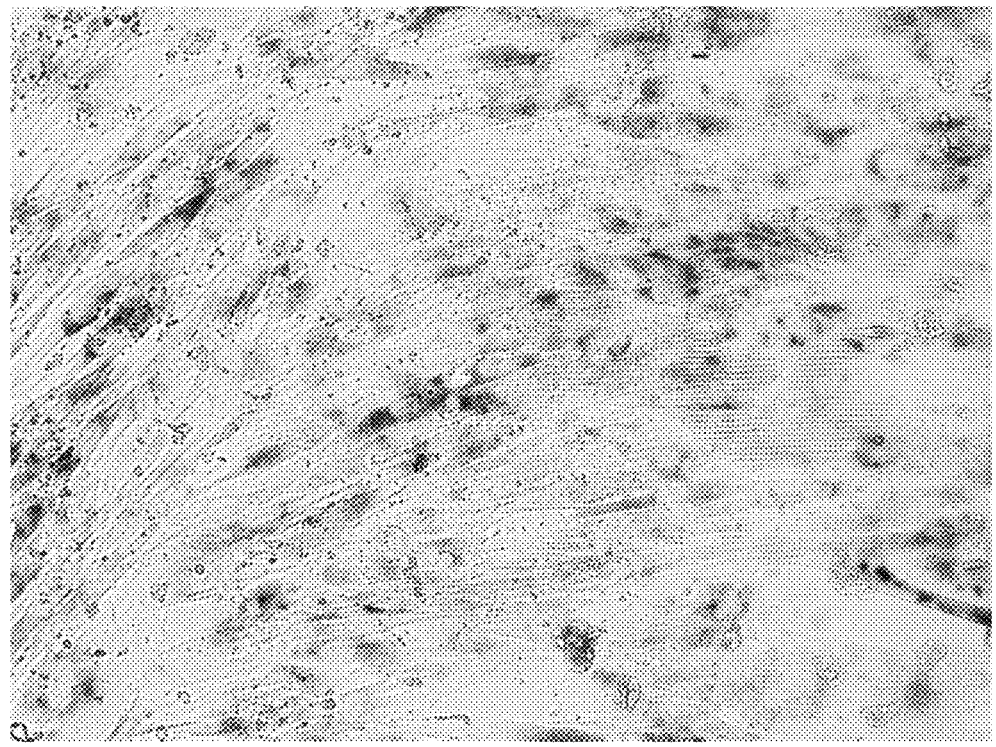
FIG. 18 show untreated treated fibroblast samples stained for beta-galactosidase.
Figure 19:
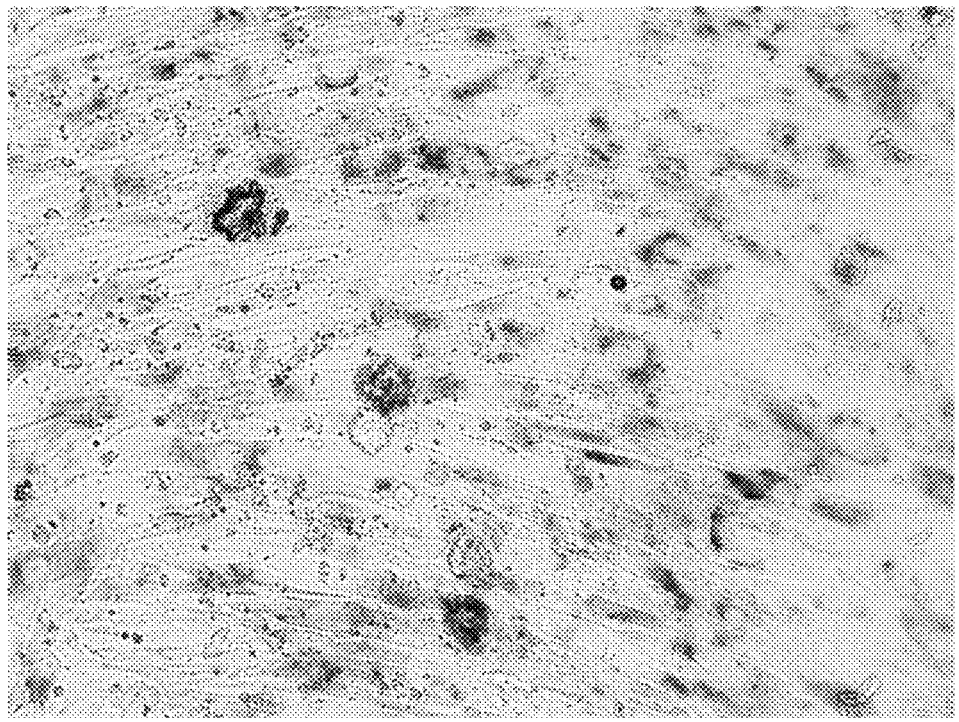
FIG. 19 show retinoic acid monotherapy treated fibroblast samples stained for beta-galactosidase.
Figure 20:
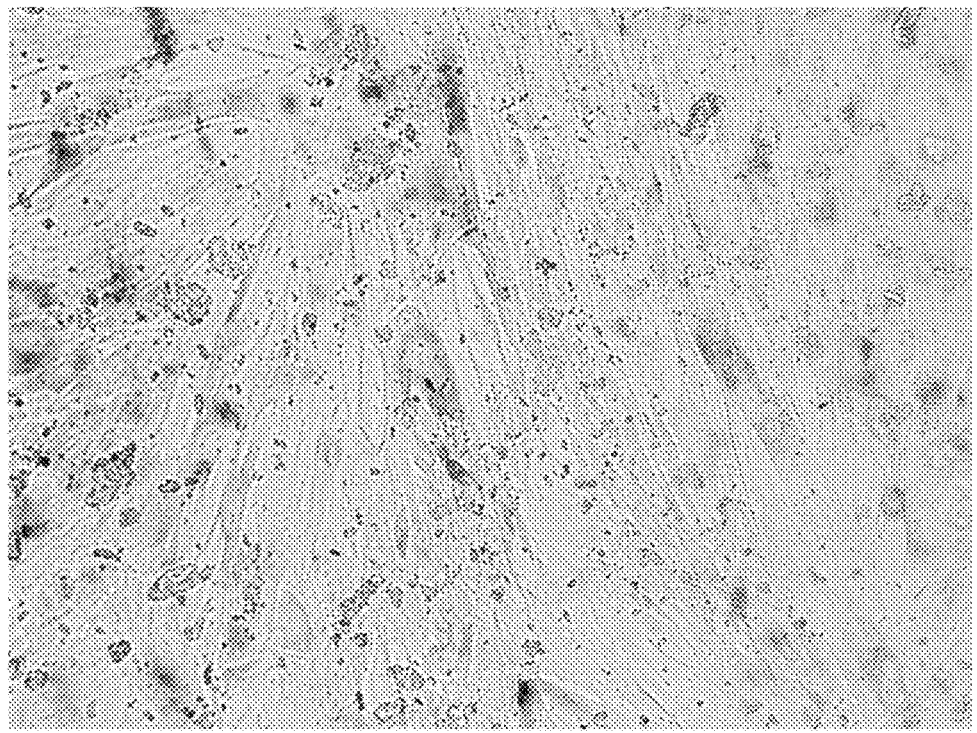
FIG. 20 show lithium, glycyrrhizic acid, and retinoic acid combination treated fibroblast samples stained for beta-galactosidase.
Figure 21:
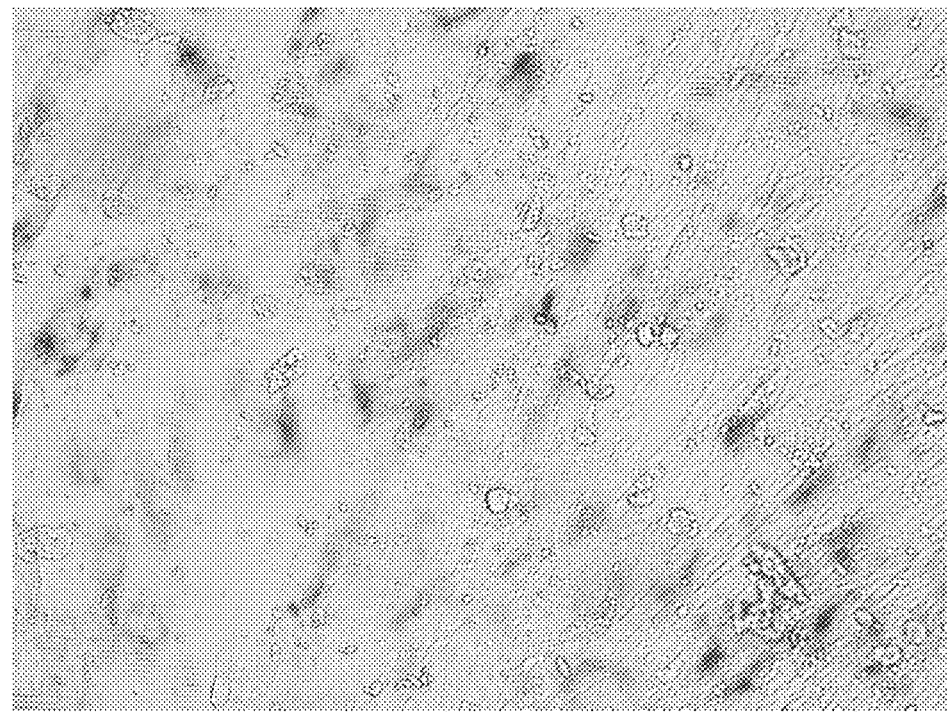
FIG. 21 show lithium and glycyrrhizic acid combination treated fibroblast samples stained for beta-galactosidase.

After staining, the flasks were examined by light microscope under 100× magnification 100× and visually evaluated and scored for visible positive beta-Galactosidase staining. FIG. 18 shows a picture of the staining results for the control group (non-treated fibroblasts stained positively for beta-Galactosidase). FIG. 19 shows a picture of the staining results for the retinoic acid mono-treated fibroblasts stained positively for beta-galactosidase. FIG. 20 shows a picture of the staining results for the fibroblasts treated with a combination of lithium carbonate, glycyrrhizic acid, retinoic acid, and stained positively for beta-galactosidase. FIG. 21 shows a picture of the staining results for the lithium carbonate and glycyrrhizic acid treated fibroblasts stained positively for beta-galactosidase.

As the data show, the groups treated with both of lithium and glycyrrhizic acid show significantly less positive staining for beta-galactosidases in comparison with the non-treated control. This effect was more prominent when adding of 1 uM of retinoic acid. The retinoic acid monotherapy flask did not show significant difference from the control group.

6. QPCR Measurement of Telomere Length and Differential Gene Expression in a Human Volunteer In this next Example, the effect of treatment with lithium orotate and licorice root extract was further evaluated on relative telomere length and the mRNA expression of telomere associated genes—telomerase RNA component (TERC) and dyskerin—in the blood cells of healthy human volunteer.

The general study methods were as follows:

DNA and RNA was extracted using QiaAmp DNA mini kit (Qiagen) according to manufacturer's instructions. DNA samples were used to assess the relative telomere length by qPCR using previously published method (Cawthon, Nucleic Acid Research, 2002). cDNA samples were used to assess mRNA expression PF markers, using qPCR, with FastStart Universal SYBR Green Master with Rox (Roche) and StepOnePlus Real-Time PCR System (Applied Biosystems). Telomere length was normalized to single copy DNA 36B4 and gene expression was normalized to the housekeeping genes HPRT. All data were analyzed using comparative $2^{-\Delta\Delta Ct}$ method. Table 6 shows the primer sets that were used:

TABLE 6

| Telomere length | h-Tel (F) | CGGTTTGTTTGGGTTTGGGTTTGGGTTTGG G TTTGGGTT SEQ ID NO: 7 | |
| | h-Tel (R) | GGCTTGCCTTACCCTTACCCTTACCC TTACCCTTACCCT SEQ ID NO: 8 | |
| Dyskerin (DKC1) | DKC1 (F) | AAAGACCGGAAGCCATTACAAG SEQ ID NO: 13 | telo-mers |
| | DKC1 (R) | GCCACTGAGAAGTGTCTAATTGA SEQ ID NO: 14 | telo-mers |
| Telomerase RNA component (TERC) | TERC (F) | CCGCTGTTTTTCTCGCTGAC SEQ ID NO: 15 | telo-mers |

Figure 22:
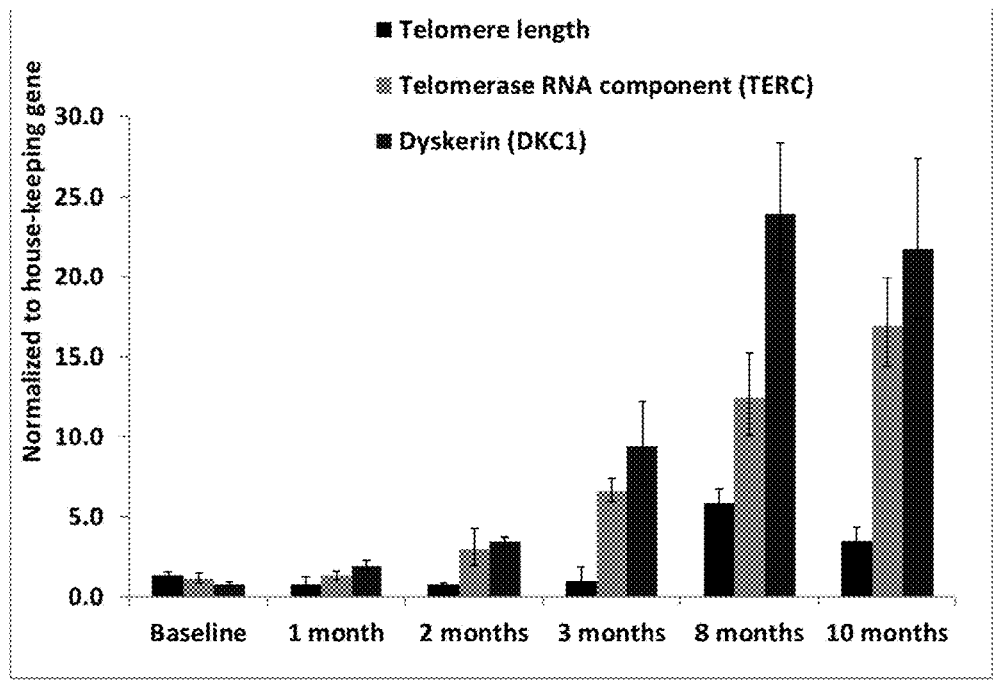
FIG. 22 shows a graph showing blood telomere related gene expression data following oral administration of lithium and glycyrrhizic acid combination.
Figure 23:
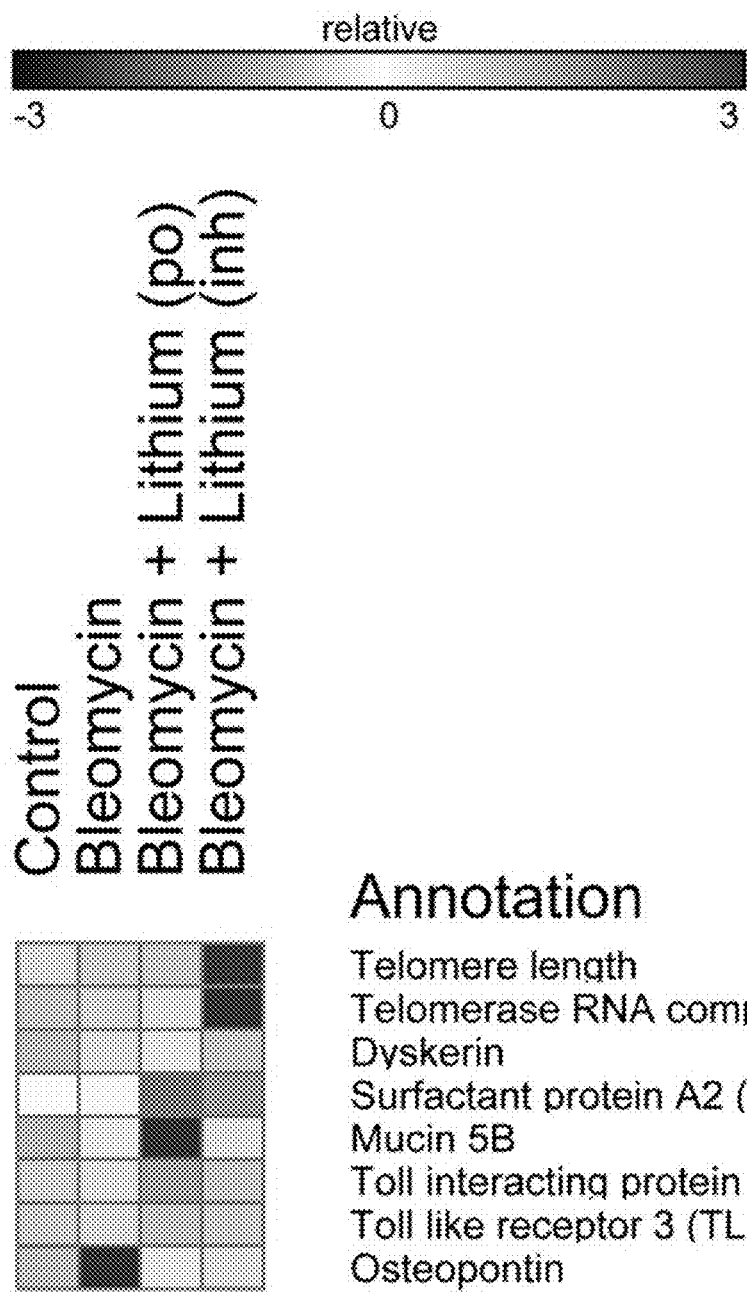
FIG. 23 shows a heatmap showing the effect of inhaled lithium on telomere lengthening.

FIG. 22 summarizes data obtained following real time analysis of blood cells from the healthy human volunteer. FIG. 23 shows a heatmap outlining the effect of inhaled lithium on telomere lengthening. As the data shows, administration of lithium/licorice combination increased the average telomere length by 3-fold in comparison to the same individual baseline. Moreover, the level of telomerase components, known to play a physiological role in the 3' elongation of telomeres via addition of TTAGGG-TERC and dyskerin—were elevated as well. As shown in FIG. 23, an increase in TERC and dyskerin was observed with contrasting reduction in the expression of fibrosis-associated genes.

7. Gene Expression of Aging Biomarkers

In this next Example, the effect of treatment with lithium orotate and glyccyrhizic acid was further evaluated on 8 signature biomarkers (4 upregulated and 4 downregulated) of aging, as identified in leading research groups in the field (Magalhaes et al, Gene Expression, 2009).

The genes overexpressed by aging examined were:

Alipoprotein D (APOD)—is associated with neurological disorders and nerve injury Fc fragment of IgG, low affinity II b (FCGR2B)—ligation to B cells downregulates antibody production and may, in some circumstances, promote apoptosis Complement component 3 (C3)—plays a central role in the activation of the complement system Clusterin (CLU)—a chaperone associated with the clearance of cellular debris and apoptosis The genes suppressed by aging examined were:

Transferrin receptor (TFRC)—is required for iron import from transferrin into cells by endocytosis Collagen type III (COL3)—found in found in extensible connective tissues such as skin, lung, and the vascular system ATP synthase (ATP5G3)—generates energy in the mitochondria (ATP from ADP)

NADH dehydrogenase (NDUFB11)—participates in mitochondrial oxidative phosphorylation.

The general study methods were as follows:

(Thermo Scientific Nunc Nunclon Delta Surface 12.5 cm; Cat. No. 136196) with McCoy's 5A complete medium were seeded with cell culture of CRL1790 (ATCC) and were kept at 37° C.; 5% $CO_2$ in incubator until 100% confluence was reached (2 days)

Figure 24:
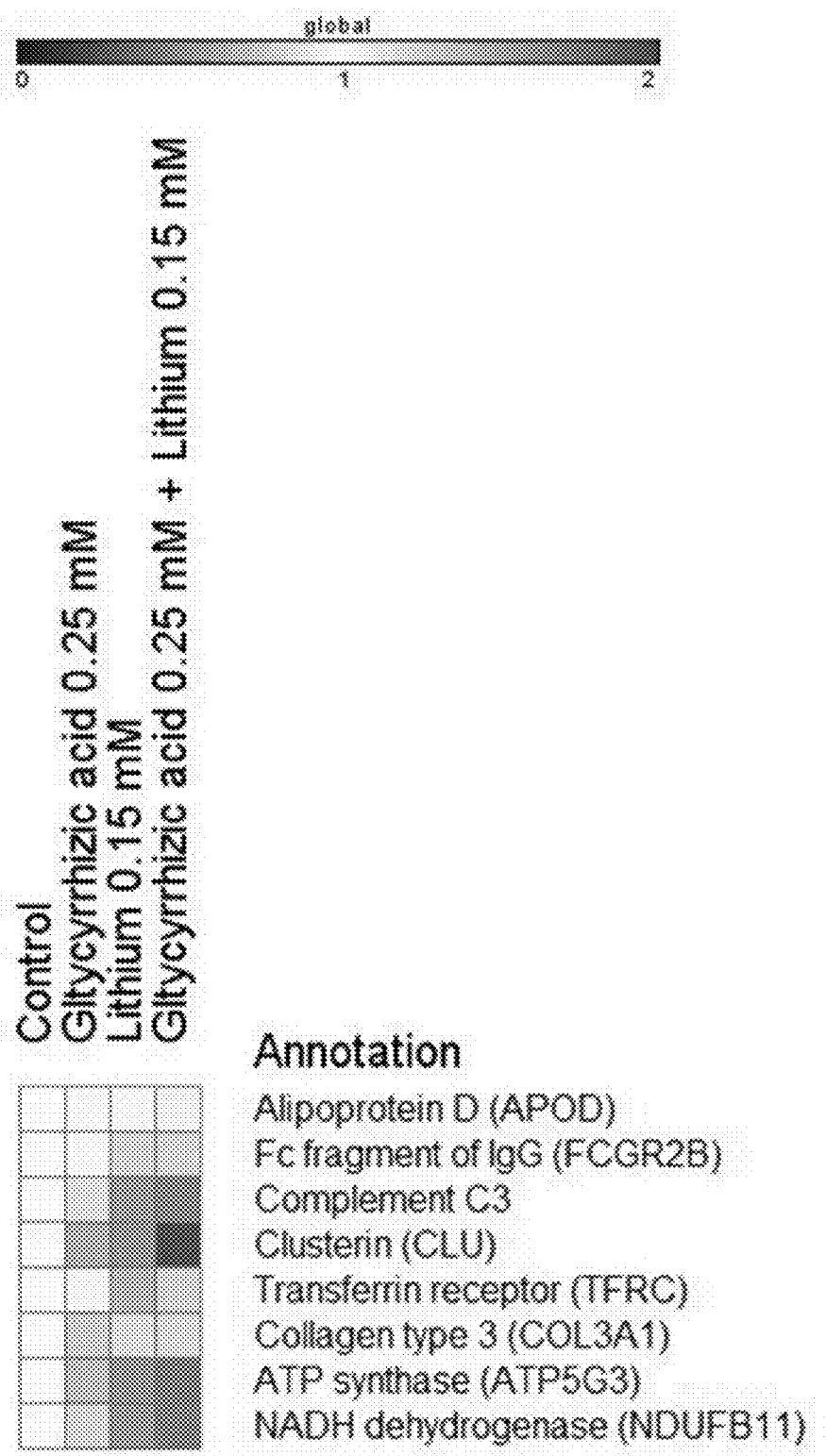
FIG. 24 shows a heatmap showing results of the effect of lithium and glycyrrhizic acid combination on gene expression of various biomarkers.

To 80 $cm^2$ flasks with CRL-1790 cells in confluence about 50-60%, McCoy's medium with 10% of FCS lithium carbonate (SigmaAldrich Cat#62472) was added in order to establish concentration of 10 μM, for 48 hours. Cells from both flasks, treated by lithium carbonate alone, glyccyrhizic acid alone and combination of both and control were detached by exposition to 5 ml of Trypsin EDTA. Flasks were then placed to incubate at 37° C., 5%-CO2 for 10 min and collected to 15 ml sterile tubes. Next, the cells were centrifuged at 600 rpm for 10 minutes; supernatant discarded and 0.1 ml pellet of density $2\times10^6$ cells/ml was dissolved in 0.5 ml of Tri reagent. Total RNA was extracted using TRI-reagent PureLink RNA Mini Kit (Life Technologies) and reverse transcribed using PrimeScript RT Master Mix (Clontech). cDNA was diluted 1:25 and used for real-time qPCR with FastStart Universal SYBR Green Master with Rox (Roche) and StepOnePlus Real-Time PCR System (Applied Biosystems). FIG. 24 shows the results of the real-time PCR.

As the data show, in CRL179 cells, 0.25 mM glyccyrhizic acid+0.15 uM lithium exhibited the most robust effect on Complement C3 and Clusterin—significantly reducing their levels, which are regularly elevated with aging. Increased levels of ATP synthase and NADH dehydrogenase were also observed, which are regularly reduced by aging. Other genes did not show significantly altered expression. The data suggests that 0.25 mM glyccyrhizic acid+0.15 uM lithium contributed to rejuvenation of cells, boosting their mitochondrial activity and suppressing inflammation. Without wishing to be bound by a particular theory, it is believed that lithium and the active component of licorice alters molecular profile, shifting cells toward a more youthful state.

It will be apparent to those skilled in the art that various modifications and variations can be made in the present invention without departing from the scope or spirit of the invention. Other aspects of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A pharmaceutical composition comprising an effective amount of at least one lithium compound selected from lithium chloride, lithium bromide, lithium carbonate, lithium nitrate, lithium sulfate, lithium acetate, lithium lactate, lithium citrate, lithium aspartate, lithium gluconate, lithium malate, lithium ascorbate, lithium orotate, lithium succinate, and combinations thereof; an effective amount of at least one glycyrrhizic triterpenoid compound selected from glycyrrhizin, enoxolone, carbenoxolone, cicloxolone, and combinations thereof, or a pharmaceutically acceptable salt thereof; and an effective amount of at least one retinoic acid compound or a pharmaceutically acceptable salt thereof;

wherein the composition is formulated for oral administration.

2. The composition of claim 1, wherein the least one lithium compound, is selected from lithium chloride, lithium bromide, lithium carbonate, lithium nitrate, lithium sulfate, lithium acetate, lithium lactate, lithium citrate, lithium aspartate, lithium malate, lithium ascorbate, lithium orotate, and combinations thereof; and the at least one glycyrrhizic triterpenoid compound is selected from glycyrrhizin, pharmaceutically acceptable salts thereof, and combinations thereof.

3. The composition of claim 1, wherein the at least one retinoic acid compound is selected from all-trans-retinoic acid, 7-cis-retinoic acid, 9-cis-retinoic acid, 11-cis-retinoic acid, and 13-cis-retinoic acid.

4. The composition of claim 1, wherein the effective amount of the lithium compound is from about 0.1 mg to about 100 mg and the effective amount of the glycyrrhizic triterpenoid compound is from about 0.1 to about 100 mg.

5. The composition of claim 1, wherein the effective amount of the lithium compound is from about 1 mg to about 50 mg and the effective amount of the glycyrrhizic triterpenoid compound is from about 1 mg to about 50 mg.

6. The composition of claim 1, wherein the effective amount of the lithium compound is from about 1 mg to about 25 mg and the effective amount of the glycyrrhizic triterpenoid compound is from about 1 mg to about 50 mg.

7. The composition of claim 1, wherein the composition is effective to reduce a beta-galactosidase level in a cell.

8. The composition of claim 1, wherein the composition is effective to reduce gene expression of at least one of Apolipoprotein D (APOD), Complement component 3 (C3), and Clusterin (CLU).

9. The composition of claim 1, wherein the composition is effective to increase gene expression of at least one of ATP synthase and NADH dehydrogenase.

10. The composition of claim 4, wherein the composition is effective to reduce a beta-galactosidase level in a cell.

11. The composition of claim 4, wherein the composition is effective to reduce gene expression of at least one of Apolipoprotein D (APOD), Complement component 3 (C3), and Clusterin (CLU).

12. The composition of claim 4, wherein the composition is effective to increase gene expression of at least one of ATP synthase and NADH dehydrogenase.

* * * * *